United States Patent [19]

Hechenbleikner et al.

[11] 3,959,220

[45] May 25, 1976

[54] POLYMER ADDITIVES COMPRISING TRANSITION METAL COMPLEXES WITH TRIVALENT PHOSPHOROUS COMPOUNDS

[75] Inventors: Ingenuin Hechenbleikner, Park Ridge, N.J.; Thomas G. Kugele, Cincinnati; John F. Hussar, Loveland, both of Ohio

[73] Assignee: Cincinnati Milacron Chemicals, Inc., Reading, Ohio

[22] Filed: Dec. 16, 1971

[21] Appl. No.: 208,927

Related U.S. Application Data

[62] Division of Ser. No. 84,494, Oct. 27, 1970, Pat. No. 3,661,843.

[52] U.S. Cl.............. 260/45.75 N; 8/83; 8/89 R; 8/171; 8/180; 106/15 FP; 260/45.75 C; 260/45.75 R; 260/45.75 P; 260/429 R; 260/438.1; 260/439 CY
[51] Int. Cl.$^2$............................................ C08J 3/20
[58] Field of Search......... 260/439, 45.75 N, 937 R, 260/930; 8/83, 89, 171, 180

[56] References Cited
UNITED STATES PATENTS

| | | | |
|---|---|---|---|
| 2,834,798 | 5/1958 | Hechenbleikner | 260/930 |
| 3,149,181 | 9/1964 | Warren | 260/937 |
| 3,152,158 | 10/1964 | Clark | 260/439 |
| 3,415,906 | 12/1968 | Shepard et al. | 260/937 |
| 3,647,841 | 3/1972 | Kauder | 260/439 |

*Primary Examiner*—V. P. Hoke
*Attorney, Agent, or Firm*—Cushman, Darby & Cushman

[57] ABSTRACT

Ultraviolet light absorbers and stabilizers, particularly for monolefin polymers, are provided from metal complexes of trivalent phosphorus compounds of the formulae

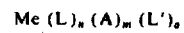

where Me is preferably nickel but can be manganese, iron, copper, molybdenum or tungsten, L is P(X)(Y)(Z) where any one or all of X, Y and Z can be O hydrocarbyl,

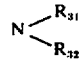

where $R_{31}$ and $R_{32}$ are hydrocarbyl oro hydrogen, S hydrocarbyl, hydrocarbyl, 2 or 3 of X, Y and Z can form one or more heterocyclic rings with P, A is an anion such as halogen, e.g. Cl, Br, I or F, $NO_3$, $ClO_4$, $R_{33}COO^-$ where $R_{33}$ is hydrocarbyl, any hydrocarbyl group can have 1 or 2 halogen substituents, m is 0 or a small whole number, e.g. 1,2,3,4, L' is CO, NO, CN, halogen, *o* is zero or a small whole number, e.g. 1,2,3,4, *n* is 1 or another small whole number, e.g. 2,3,4, *o+m+n* is not greater than the highest coordination number of the metal.

14 Claims, No Drawings

POLYMER ADDITIVES COMPRISING TRANSITION METAL COMPLEXES WITH TRIVALENT PHOSPHOROUS COMPOUNDS

This is a division of application Ser. No. 84,494 filed Oct. 27, 1970 now U.S. Pat. No. 3,661,843.

The present invention relates to stabilizers and ultraviolet absorbers for plastics. The compounds all are metal complexes of trivalent phosphorus compounds of the formulae $Me(L)_n(A)_m(L')_o$ where Me is preferably nickel but can be manganese, iron, copper, molybdenum or tungsten, L is $P(X)(Y)(Z)$ where any one or all of X, Y and Z can be O hydrocarbyl,

where $R_{31}$ and $R_{32}$ are hydrocarbyl or hydrogen, S hydrocarbyl, hydrocarbyl, 2 or 3 of X, Y and Z can form one or more heterocyclic rings with P, A is an anion such as halogen, e.g. Cl, Br, I or F, $NO_3$, $ClO_4$, $R_{33}COO^-$ where $R_{33}$ is hydrocarbyl, any hydrocarbyl group can have 1 or 2 halogen substituents, m is 0 or a small whole number, e.g. 1,2,3,4, L' is CO, NO, CN, halogen, o is zero or a small whole number, e.g. 1,2,3,4, n is 1 or another small whole number, e.g. 2,3,4, $o+m+n$ is not greater than the highest coordination number of the metal.

While all of the compounds employed in the present invention come within the above generic formula, the compounds are not equally useful and not all compounds within the generic formula can be employed. The disclosure and claims hereinafter will point out which compounds can be used. Some of the compounds not only are novel as stabilizers and ultraviolet absorbers, but also are novel per se.

The preferred compounds are the nickel complexes and they are particularly useful with monoolefin polymers such as polypropylene, polyethylene, and copolymers of ethylene or propylene with each other or with other ethylenically unsaturated hydrocarbons.

BACKGROUND

It has been proposed in Kauder U.S. Pat. No. 3,395,112, July 30, 1968 discloses certain nickel organophosphites as stabilizers for olefin polymers. In addition, ultraviolet light absorbers and thiodipropionates or organotriphosphites can be employed. Such materials are not nickel complexes with trivalent phosphorus compounds. Kauder, on col. 3, lines 11-20, shows that nickel forms two types of compounds in one of which the nickel is attached to organic radicals by coordinate bonds in which nickel has an apparent valence of four and in the other of which the bonds are ionic and the nickel is bivalent. Kauder mentions that only the latter type compounds have been found to be stabilizers for polyolefins. No mention is made of coordination complexes where nickel has a valence of 0 or a positive valence, e.g. of two.

Salts of nickel (and other metals) with organic phosphites having a free hydroxyl group of course, are well known as antioxidants for polyolefins, e.g. note Kiyawa U.S. Pat. No. 3,412,118, Nov. 19, 1968, Marinaccio U.S. Pat. No. 3,481,897 Dec. 2, 1969. These compounds are not coordination complexes.

The use of a special type of trivalent organo phosphorus copper complex as flame retardants for polymers including polyethylene is proposed in Grayson U.S. Pat. No. 3,294,870, Dec. 27, 1966 and Grayson U.S. Pat. No. 3,345,392, Oct. 3, 1967. The Grayson complexes are complexes of cuprous salts with ethylene bis(aryl or cyanoethyl phosphines). There is no indication of improved ultraviolet light stability.

KNOWN COMPLEXES OF NICKEL, MANGANESE, MOLYBDENUM, IRON, COPPER AND TUNGSTEN WITH TRIVALENT PHOSPHORUS COMPOUNDS USEFUL IN THE INVENTION

There are many patents and literature articles showing the preparation or mentioning various uses of trivalent organic phosphorus compounds useful in the present invention. They are set forth below. The entire disclosure of these patents and literature references is hereby incorporated by reference rather than being repeated verbatim to reduce the size of the present application. The metal complexes of organic trivalent phosphorus compounds useful in the present invention can be manufactured by the methods disclosed in such prior art or by the specific procedures set forth as methods A and D hereinafter.

Kleinschindt U.S. Pat. No. 2,542,417, Feb. 20, 1951, discloses bis(triphenyl phosphine) nickel dicarbonyl complex. Reed U.S. Pat. No. 2,686,208, Aug. 10, 1954, discloses various aryl and alkyl phosphine nickel carbonyl complexes and a method of making them including bis(triphenyl phosphine) nickel dicarbonyl, mono (triaryl phosphine) nickel tricarbonyl and bis(trialkyl phosphine) nickel dicarbonyl. Reppe U.S. Pat. No. 2,738,364, Mar. 13, 1956, discloses tertiary phosphine nickel salts such as the chlorides, bromides, iodides, cyanide and rhodanides, including bis(triphenyl phosphine) nickel dibromide. Hodes U.S. Pat. No. 3,054,775, Sept. 18, 1962, discloses various alkyl and aryl phosphine nickel complexes including bis(tributyl phosphine) nickel dichloride, bis(tributyl phosphine) nickel dicarbonyl, bis(biphenyl phosphine) nickel dicarbonyl. Schroll U.S. Pat. No. 2,054,815, Sept. 18, 1962, discloses the preparation of cyclopentadienyl nickel trihydrocarbyl phosphine complexes including cyclopentadienyl nickel triphenyl phosphine chloride, cyclopentadienyl nickel trimethyl chloride, cyclopentadienyl nickel triethyl phosphine chloride, cyclopentadienyl nickel triisobutyl phosphine chloride, cyclopentadienyl nickel triethyl phosphine iodide, cyclopentadienyl nickel triphenyl phosphine bromide, cyclopentadienyl nickel tri(m-tolyl) phosphine iodide, cyclopentadienyl nickel tri(p-tolyl) phosphine bromide, methylcyclopentadienyl nickel biphenyl phosphine chloride, ethylcyclopentadienyl nickel triethyl phosphine bromide, methyl t-butyl-cyclopentadienyl nickel trioctyl phosphine chloride and indenyl nickel triphenyl phosphine chloride.

Luttinger U.S. Pat. No. 3,098,843, July 23, 1963 and Luttinger U.S. Pat. No. 3,131,155, Apr. 28, 1964, both show the preparation of aliphatic and aromatic phosphine nickel complexes including bis(tris cyanoethyl phosphine) nickel dibromide, bis(tris cyanoethyl phosphine) nickel dichloride, bis(triphenyl phosphine) nickel dichloride, bis(tributyl phosphine) nickel dichloride ethane bis(di[cyanoethyl]phosphine) nickel dichloride, bis(triphenyl phosphine) nickel dirhodanide, bis(tris cyanoethyl phosphine) nickel sulfate and bis(tris cyanoethyl phosphine) tri nickel diphosphate.

Meriwether U.S. Pat. No. 3,117,952, Jan. 14, 1964, discloses nickel carbonyl mono and bis phosphine complexes having alkyl, aryl, alkoxy, aryloxy and cyanoalkyl groups attached to the phosphorus including dicarbonyl bis [tris (2-cyanoethyl phosphine)] nickel, dicarbonyl tetrakis (2-cyanoethyl) diphosphine nickel, dicarbonyl bis (triphenyl phosphine) nickel, dicarbonyl tetrakis-(2-cyanoethyl) ethylene diphosphine nickel, dicarbonyl tetraethyl ethylene diphosphine nickel dicarbonyl bis(phenyl diethyl phosphine)nickel tricarbonyl phenyl diethyl phosphine nickel.

Clark U.S. Pat. No. 3,152,158, Oct. 6, 1964, discloses the preparation of tetrakis (tri organophosphite) nickel complexes of the formula Ni[P(OR$_1$)(OR$_2$)(OR$_3$)]$_4$ where R$_1$ and R$_2$ and R$_3$ are alkyl, substituted alkyl, cycloalkyl, substituted cycloalkyl, aryl substituted aryl and arakyl including tetrakis (triphenyl phosphite) nickel, tetrakis [tri(2-ethylhexyl) phosphite] nickel, tetrakis [tri(p-methoxyphenyl) phosphite] nickel, tetrakis [tri(p-tolyl)phosphite] nickel, tetrakis [tri(2-chloroethyl) phosphite] nickel, triphenyl phosphite nickel tricarbonyl, bis(triphenyl phosphite) nickel dicarbonyl, tri(triphenyl phosphite) nickel monocarbonyl, tetrakis (tris octadecyl phosphite) nickel, tetrakis (trimethyl phosphite) nickel, tetrakis (tricyclohexyl phosphite) nickel, tetrakis (tricyclopentyl phosphite) nickel.

Clark U.S. Pat. No. 3,244,738, Apr. 5, 1966, shows the preparation of various phosphine nickel carbonyl complexes including tris(triphenyl phosphine) nickel monocarbonyl, tris(triphenyl phosphite) nickel monocarbonyl, bis(triphenyl phosphite) nickel dicarbonyl, tris(tri p-tolylphosphite) nickel monocarbonyl, tris (tri-2-chloroethyl phosphite) nickel monocarbonyl, tris(tricyclohexyl phosphine) nickel monocarbonyl, bis(triphenyl phosphite) tritolyl phosphite nickel monocarbonyl, bis(triphenyl phosphite) triethyl phosphite nickel monocarbonyl, tris(mixed 2-ethylhexyl octyl phenyl phosphite) nickel monocarbonyl, bis(triphenyl phosphite) triphenyl phosphine nickel monocarbonyl, bis (triphenyl phosphine) triphenyl phosphite nickel monocarbonyl. Cities Service British Pat. No. 979,553, Jan. 6, 1965, has a similar disclosure.

Storrs U.S. Pat. NO. 3,249,641, May 3, 1966, shows various trivalent phosphorus nickel carbonyl complexes including triphenyl phosphite nickel tricarbonyl, bis (triphenyl thiophosphite) nickel dicarbonyl, bis(tritolyl phosphite) nickel dicarbonyl, tris(triisooctyl phosphite) nickel carbonyl, bis(triphenyl phosphine) nickel dicarbonyl, bis(phenyl diethyl phosphine) nickel dicarbonyl, bis(ethyl dipropyl phosphine) nickel dicarbonyl.

Cannell U.S. Pat. No. 3,271,438, Sept. 6, 1966, discloses tetrakis (trihydrocarbyl phosphite) nickel (O) compounds including tetrakis (tributyl phosphite nickel (O), tetrakis (triphenyl phosphite) nickel (O), tetrakis [tri(p-tolyl) phosphite] nickel (O), tetrakis (trimethyl phosphite) nickel (O), tetrakis (triisopropyl phosphite) nickel (O), bis(tritolyl phosphite), bis(trihexyl phosphite) nickel (O), tetrakis (amyldibutyl phosphite) nickle (O), tetrakis (dibenzylphenyl phosphite) nickel (O), tetrakis [tri(2-ethylhexyl) phosphite] nickel (O).

Clark U.S. Pat. No. 3,328,443, June 27, 1967, discloses the preparation of tetrakis(organo phosphorus) nickel complexes including tetrakis (triphenyl phosphite) nickel, tetrakis(tri-p-methoxyphenyl phosphite) nickel, tetrakis (tri-p-tolyl) phosphite] nickel, tetrakis [tri(2-ethylhexyl) phosphite] nickel, bis(triphenyl phosphite) bis(triethyl phosphite) nickel, tris (triphenyl phosphite) triphenyl phosphine nickel as well as other compounds having the formula

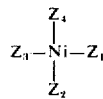

where Z$_1$, Z$_2$, Z$_3$ and Z$_4$ are P(O$_a$R$_1$)(O$_a$R$_2$)(O$_a$R$_3$) where $a$ is 0 or 1 and R$_1$, R$_2$ and R$_3$ are alkyl, cycloalkyl, aryl, alkaryl, alkyl substituted cycloalkyl, aralkyl, alkoxyphenyl, alkoxyalkyl, hydroxyphenyl, alkoxy, haloaryl, haloalkyl and halocycloalkyl.

Kutepaw U.S. Pat. No. 3,346,608, Oct. 10, 1967, discloses the preparation of complexes such as tris(triphenylphosphite) nickel, tris(tri-m-tolylphosphite) nickel, bis(tri-thymyl phosphite) nickel, bis(tri-o-diphenyl phosphite) nickel, bis(tri-2,4-di-t-butylphenyl phosphite) nickel, bis(tri-4-t-butylphenyl phosphite) nickel, tris(tri-o-chlorophenyl phosphite) nickel, bis(-tri-4-isooctyl phenyl phosphite) nickel.

Maxfield U.S. Pat. No. 3,427,365, Feb. 11, 1969, discloses nitrosyl nickel complexes including triphenyl phosphine (nitrosyl) iodonickel, triphenyl phosphine (nitrosyl) bromonickel, tributyl phosphine (nitrosyl) chloronickel, tricyclopentyl phosphine (nitrosyl) chloronickel.

Vinal, Inorganic Chemistry, Vol. 3, (7) July 1964, pages 1062–1063 discloses the preparation of tetrakis (trialkyl phosphite) nickel (O) complexes such as tetrakis (triethyl phosphite) nickel (O).

Gmelin's Handbuch Der Anorganischen Chemie, 8th edition, System No. 57 (C), pages 10-35 shows the preparation of numerous complexes of trivalent phosphorus compounds with nickel, e.g. tetrakis (triaminophosphine) nickel, tetrakis (triethyl phosphine) nickel, bis(triethyl phosphine) nitrosyl nickel nitrite, bis(-triethyl phosphine) nitrosyl nickel nitrate, bis(triethyl phosphine) nitrosyl nickel chloride, bis(triethyl phosphine) nitrosyl nickel bromide, bis(triethyl phosphine) nitrosyl nickel iodide, bis(tricyclohexyl phosphine) nitrosyl nickel bromide, bis(tricyclohexyl phosphine) nitrosyl nickel thiocyanate, cis-bis(tricyclohexyl phosphine nitrosyl nickel bromide), trans-bis(tricyclohexyl phosphine nitrosyl nickel bromide), tetrakis (triphenyl phosphine) nickel, tris(triphenyl phosphine) nickel, bis(triphenyl phosphine) nitrosyl nickel nitrite, bis(-triphenyl phosphine) nitrosyl nickel nitrate, bis(triphenyl phosphine) nitrosyl nickel chloride, bis(triphenyl phosphine) nitrosyl nickel bromide, bis(triphenyl phosphine) nitrosyl nickel iodide, trans bis(triphenyl phosphine nitrosyl nickel iodide), bis(triphenyl phosphine nitrosyl nickel thiocyanate), bis(ethyl diphenyl) nickel dicarbonyl, bis(ethyl diphenyl) nitrosyl nickel bromide, bis(ethane bis[dimethylphosphine]) nickel, bis (methane bis[diphenyl phosphine]) nickel, bis(ethane bis[-diphenyl phosphine]) nickel, ethane bis(diphenyl phosphine) nitrosyl nickel iodide, ethane bis(diphenyl phosphine) nitrosyl nickel thiocyanate, bis(tricyclohexyl phosphine) nickel nitrosyl bromide ethane bis(diphenyl phosphine), bis(propane bis[diphenyl phosphine]) nickel, bis(o-phenylene bis[diethyl phosphine]) nickel, bis(o-phenylene bis[diphenyl phosphine]) nickel, ethane bis(diphenyl phosphine) nickel dicarbonyl, o-phenylene bis(diethyl phosphine) nickel dicarbonyl, o- phenylene bis(diphenyl phosphine) nickel dicarbonyl, 1,1,1-tris(diphenylphosphinomethyl) ethane nickel monocarbonyl, bis[1,1,1-tris(diphenylphosphinomethyl) ethane] nickel, trimethyl phosphite nickel tricarbonyl, bis (trimethyl phosphite) nickel dicarbonyl, tris(trimethyl phosphite) nickel monocarbonyl, tetrakis(trimethyl phosphite) nickel, triethyl phosphite nickel tricarbonyl, bis(triethyl phosphite) nickel dicarbonyl, tris(triethyl phosphite) nickel monocarbonyl, tetrakis(triethyl phosphite) nickel, tetrakis [tris-(2-chloroethyl) phosphite] nickel, tetrakis(tripropyl phosphite), nickel, tetrakis (triisopropyl phosphite) nickel, tetrakis(tributyl phosphite) nickel, tetrakis (tris[2-ethylhexyl] phosphite) nickel, tetrakis (tris[2-ethoxyhexyl] phosphite) nickel, tetrakis (tris[decyl] phosphite) nickel, tetrakis (tricyclohexyl phosphite) nickel, tetrakis (triphenyl phosphite) nickel, tris(-triphenyl phosphite) nickel monocarbonyl, bis(triphenyl phosphite) nickel dicarbonyl, triphenyl phosphite nickel tricarbonyl, bis(triphenyl phosphite) di nitrosyl nickel, bis(triphenyl phosphite) nitrosyl nickel bromide, bis(triphenyl phosphite) nitroxyl nickel iodide, trans bis[bis(triphenyl phosphite) nitrosyl nickel bromide], trans bis[bis(triphenyl phosphite)nitrosyl nickel iodide], bis (triphenyl phosphite) nitrosyl nickel thiocyanate, tris (triphenyl phosphite)triphenyl phosphine nickel, bis (triphenyl phosphite) bis(triethyl phosphite) nickel, tetrakis (diphenyl decyl phosphite) nickel, tetrakis (p-tolyl phosphite) nickel, tetrakis (trimethylol ethane phosphite) nickel (also called tetrakis (4-methyl-2,6,7-trioxa-1-phospha-bicyclo[2,2,2]octane)
nickel, tris (trimethylol ethane phosphite) nickel carbonyl, bis (trimethylol ethane phosphite) nickel dicarbonyl, trimethylol ethane phosphite nickel tricarbonyl, tetrakis (trimethylol propane phosphite) nickel, bis(-triphenyl phosphine) nickel chloride, bis(triphenyl phosphine) nickel bromide, bis(triphenyl phosphine)-nickel iodide, tris (triphenyl phosphine) nickel chloride, tris (triphenyl phosphine) nickel bromide, tris (triphenyl phosphine)nickel iodide.

Adelson U.S. Pat. No. 2,645,613, July 14, 1953, discloses cupric chloride tributyl phosphine complex, Cannell U.S. Pat. No. 3,102,899, Sept. 3, 1963, discloses the preparation of nickel, iron and molybdenum complexes such as tetrakis (triethyl phosphite) nickel (0), tetrakis (tricresyl phosphite) nickel (0), tetrakis (0,0-dimethyl phenyl thiophosphite) nickel (0), hexakis (tripentyl phosphine) molybdenum (0), tetrakis (tris[diethylamino] phosphite) nickel (0), tris (dimethylamino dimethyl thiophosphite) iron (0).

Mullineaux U.S. Pat. No. 3,110,747, Nov. 12, 1963, discloses nickel, molybdenum, tungsten, iron and manganese complexes including tetrakis (o,o-dimethyl-p-chlorophenyl thiophosphite) nickel, hexakis (dimethylamino dimethyl thiophosphite) molybdenum, hexakis (tris[2,6-dibromo-4-methylphenyl] phosphite) tungsten.

Welch U.S. Pat. No. 3,355,439, Nov. 28, 1967, prepares nickel, molybdenum, copper and iron salt complexes of vinyl phosphines of the formula $R_2PCH=CH_2$ where each R is hydrocarbyl, e.g. vinyl diphenyl phosphine copper chlorides (1:1), vinyl diphenyl phosphine nickel chloride (1:1).

Patrafke U.S. Pat. No. 3,438,805, Apr. 15, 1966, discloses nickel, copper, iron and molybdenum salt complexes such as bis(triphenyl phosphine) cupric chloride, bis(tributyl phosphine) cupric chloride, bis(-tributyl phosphine) cupric acetate, bis(tris[dimethylamino] phosphine) molybdenum trichloride, bis(-tris[dimethylamino] phosphine) iron dichloride.

Van Peski U.S. Pat. No. 2,199,944, May 7, 1940, discloses complexes of copper, nickel and iron salts with phosphines and phosphites. Raichele U.S. Pat. No. 3,360,589, Dec. 26, 1967, stabilizes gellable polyesters with cuprous chloride and bromide complexes of tertiary alkyl, cycloalkyl, aryl and aralkyl phosphites, e.g. triethyl phosphite cuprous chloride, triethyl phosphite cuprous bromide, tris(2-chloroethyl) phosphite cuprous chloride, tris(2-chloroethyl) phosphite cuprous bromide, tripropyl phosphite cuprous chloride, tripropyl phosphite cuprous bromide, tributyl phosphite cuprous chloride, tributyl phosphite cuprous bromide, tribenzyl phosphite cuprous chloride, tribenzyl phosphite cuprous bromide, tricyclohexyl phosphite cuprous chloride, tricyclohexyl phosphite cuprous bromide, triphenyl phosphite cuprous chloride and triphenyl phosphite cuprous bromide.

Dikotter U.S. Pat. No. 3,428,597, stabilizes polyamides with cuprous iodide complexes of alkyl and aryl phosphines and phosphites such as triphenyl phosphite cuprous iodide, tris decyl phosphite cuprous iodide, triphenyl phosphine cuprous iodide, diphenyl decyl phosphite cuprous iodide, trihexyl phosphine cuprous iodide, trihexyl phosphite cuprous iodide hexyl didecyl phosphite cuprous iodide, hexyl didecyl phosphine cuprous iodide.

Lambert U.S. Pat. No. 3,013,039, discloses the preparation of alkyl, cycloalkyl, aralkyl, aryl and alkaryl phosphine manganese tricarbonyl nitrosyl complexes and similar triorgano phosphine nitrosyl complexes, e.g. triphenyl phosphine manganese trinitrosyl, triphenyl phosphine manganese tricarbonyl nitrosyl, triethyl phosphine manganese trinitrosyl, triethyl phosphine manganese tricarbonyl mononitrosyl, tricyclohexyl phosphine manganese trinitrosyl, tricyclohexyl phosphine manganese tricarbonyl mononitrosyl, trimethylphosphine manganese tricarbonyl nitrosyl, trimethyl phosphine manganese trinitrosyl, tripropyl phosphine manganese tricarbonyl nitrosyl, tripropyl phosphine manganese trinitrosyl, tributyl phosphine manganese tricarbonyl nitrosyl, tributyl phosphine manganese trinitrosyl, tricumenyl phosphine manganese trinitrosyl, tricycloheptyl phosphine manganese tricarbonyl nitrosyl, tricycloheptyl phosphine manganese trinitrosyl, triisopropyl phosphine manganese tricarbonyl nitrosyl, tribenzyl phosphine manganese tricarbonyl nitrosyl, tribenzyl phosphine manganese trinitrosyl, tribiphenyl phosphine manganese tricarbonyl nitrosyl, tribisphenyl phosphine manganese trinitrosyl.

Johnston U.S. Pat. No. 3,037,038, May 29, 1962, shows the preparation of manganese carbonyl polytertiary phosphites such as manganese tricarbonyl bis(-triphenyl phosphite), manganese dicarbonyl tris(tributyl phosphite), manganese tricarbonyl bis(tributyl phosphite), manganese carbonyl tetrakis (trimethyl phosphite), manganese tricarbonyl bis (triethyl thiophosphite), manganese tricarbonyl bis(tritolyl phosphite), manganese tricarbonyl bis(trimethyl phosphite), manganese tricarbonyl bis(triethyl phosphite), manganese dicarbonyl tris (triethylthiophosphite), manganese carbonyl tetrakis (triethylthiophosphite), manganese carbonyl tetrakis (trinaphthyl phosphite), manganese carbonyl tetrakis (phenyl dimethyl phosphite), manganese carbonyl tetrakis (tribenzyl phosphite), manganese carbonyl bis(trimethylthiophosphite) bis(triphenylthiophosphite).

Coffield U.S. Pat. No. 3,100,212, Aug. 6, 1963, discloses complexes such as triphenyl phosphine manganese tetracarbonyl, tricyclohexyl phosphine manganese tetracarbonyl, triethyl phosphine manganese tetracarbonyl, triphenyl phosphite manganese tetracarbonyl.

Schroll U.S. Pat. No. 3,130,215, Apr. 21, 1964, discloses the preparation of organomanganese carbonyl triorganophosphines and phosphites such as methylcyclopentadienyl manganese carbonyl bis(trimethyl phosphite) cyclopentadienyl manganese dicarbonyl tributyl phosphine, methyl cyclopentadienyl manganese dicarbonyl trimethyl phosphite, cyclopentadienyl manganese carbonyl bis (triphenyl phosphite), cyclopentadienyl manganese dicarbonyl triphenyl phosphite, cyclopentadienyl manganese dicarbonyl triphenylphosphine, methyl cyclopentadienyl manganese carbonyl bis(triphenyl phosphite), methyl cyclopentadienyl manganese dicarbonyl triphenyl phosphites, methyl cyclopentadienyl manganese carbonyl bis(triphenyl phosphine), methyl cyclopentadienyl manganese dicarbonyl triphenyl phosphines, ethyl propyl cyclopentadienyl manganese dicarbonyl trianisyl phosphite, dimethyl cyclopentadienyl manganese carbonyl bis (tris-[ethylphenyl] phosphite), methyl cyclopentadienyl manganese dicarbonyl tris(propylphenyl) phosphine, octyl cyclopentadienyl manganese carbonyl bis(tri-n-hexyl phosphite), cyclopentadienyl manganese carbonyl bis(trimethyl phosphine), methyl cyclopentadienyl manganese carbonyl, bis(trimethyl phosphine), dimethyl cyclopentadienyl manganese dicarbonyl tridodecyl phosphite and cyclopentadienyl manganese dicarbonyl tri-n-propyl phosphine.

Matthews U.S. Pat. No. 3,117,983, Jan. 14, 1964, discloses the preparation of molybdenum and tungsten carbonyl phosphines and phosphites such as bis(triphenyl phosphine) molybdenum tetracarbonyl, tris(triphenyl phosphite) molybdenum, tricarbonyl, bis(triphenyl phosphite) molybdenum tetracarbonyl, triphenyl phosphine tungsten pentacarbonyl, triphenyl phosphine molybdenum pentacarbonyl.

McHugh U.S. Pat. No. 3,173,873, Mar. 16, 1965, discloses iron carbonyl phosphine complexes such as bis(triphenylphosphinyl) iron tricarbonyl, bis(tri alpha naphthyl phosphinyl) iron tricarbonyl, bis(tri beta naphthyl phosphinyl) iron tricarbonyl, bis(tri-4-tolylphosphinyl) iron tricarbonyl, triphenyl phosphinyl iron tetracarbonyl, trimesityl phosphinyl iron tetracarbonyl, tris(2-phenylethyl) phosphinyl iron tetracarbonyl, tris(4-biphenylyl) phosphinyl iron tetracarbonyl, tris(-tetrahydronaphthyl) phosphinyl iron tetracarbonyl, and diphenyl benzyl phosphinyl iron tetracarbonyl.

Unless otherwise indicated, all parts and percentages are by weight.

METHODS A, AND D

Methods A, and D were carried out as in the illustrative examples below.

Method A

Tris(tricyclohexylphosphite) Nickel[0] Carbonyl
(Compound 19)

| Reagents | | |
|---|---|---|
| Ni(CO)₄ | 34.34 g | 0.2 mol |
| (C₆H₁₁O)₃P | 262 g | 0.8 mol |
| Xylene (Solvent) | 250 ml | |

The tricyclohexyl phosphite and xylene were added to a glass apparatus fitted for heating, stirring, and refluxing. Nickel tetracarbonyl was slowly added at room temperature. After the addition was completed, the stirred reaction mixture was heated to reflux and held there until evolution of carbon monoxide ceased. The reaction flask was then cooled and the colorless crystals which separated were isolated by filtration. After drying, the colorless crystals melted at 160°–170°C. The yield was 95% based on the nickel carbonyl used.

Analysis of the product indicated 5.5% Nickel.

Method A

Tetrakis [tris(2-chloroethyl) phosphite] Nickel[0]
(Compound 20)

| Reagents | | |
|---|---|---|
| Ni(CO)₄ | 19.0 g | 0.112 mole |
| Tris(2-chloroethyl) phosphite | 134 g | 0.5 mole |
| Xylene (Solvent) | 225 ml | |

The phosphite and one-half the xylene were placed in a glass reaction vessel. To this was added the nickel carbonyl dissolved in the remainder of xylene. When addition was completed, the stirred reaction mixture was slowly heated to reflux and held there until evolution of carbon monoxide ceased. The reaction mixture was cooled slightly, then vacuum stripped at 150°C/0.1 mm. The residue, a dark solid, was first recrystallized from methanol-acetone, finally heptanebenzene. Yield: 37 gms.

Method A

Tetrakis(2,2-dimethyl-1,3-propylene cyclohexyl phosphite) Nickel[0]
(Compound 13)

| Reagents | | |
|---|---|---|
| Ni(CO)₄ | 9.2 g | 0.054 mole |
| 2,2-dimethyl-1,3-propylene cyclohexyl phosphite | 50 g | 0.22 mole |
| Chlorobenzene (solvent) | 200 ml | |

The nickel carbonyl and chlorobenzene were added to a 3-necked flask equipped with stirrer, dropping funnel and condenser. 2,2-dimethyl-1,3-propylene cyclohexyl phosphite was slowly added at room temperature After the addition was completed, the stirred mixture was slowly heated to reflux and this temperature maintained until no more CO evolved. The solvent was removed under 0.5 mm vacuum to a final temperature of 140°C. Upon cooling the flask contents solidified and the colorless crystalline compound was isolated by recrystallization from acetone. The yield was 52 g or 90% of the theoretical.

METHOD D

Bis(o-phenylenephenyl phosphite) cuprous iodide complex (Compound 14)

0.1 mol of cuprous iodide was suspended in 50 cc of acetonitrile and 0.2 mol of o-phenylenephenyl phosphite was added. The mixture was heated under reflux for 10 minutes and the crystals which separated were collected by filtration.

ILLUSTRATIVE TYPES OF COMPOUNDS USEFUL IN THE INVENTION

Type 1

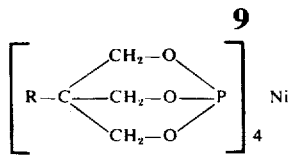

where R is alkyl of 1 to 17 carbon atoms, preferably 1 to 4 carbon atoms, e.g. nickel⁰ tetrakis (trimethylolpropane phosphite) (hereinafter identified as Compound 1), nickel tetrakis (trimethylolethane phosphite), nickel tetrakis (trimethylolbutane phosphite), nickel tetrakis (trimethylol isobutane phosphite), nickel tetrakis (trimethylol pentane phosphite), nickel tetrakis (trimethylol hexane phosphite), nickel tetrakis (trimethylol heptadecane phosphite), nickel tetrakis (trimethylol undecane phosphite).

Type 2

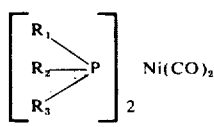

where $R_1$, $R_2$ and $R_3$ are hydrocarbyl, e.g. aryl, alkyl, cycloalkyl or aralkyl, e.g. bis(triphenylphosphine) nickel⁰ dicarbonyl (hereinafter called Compound 2), bis(trimethylphosphine) nickel dicarbonyl, bis(triethylphosphine) nickel dicarbonyl, bis (tributyl phosphine) nickel dicarbonyl, bis(tricyclohexyl phosphine) nickel dicarbonyl, bis(tri-[2-ethylhexyl] phosphine) nickel dicarbonyl, bis(tri[octadecyl] phosphine) nickel dicarbonyl, bis(tri[p-tolyl] phosphine) nickel dicarbonyl, bis(tribenzyl phosphine) nickel dicarbonyl, bis(tri dodecyl phosphine) nickel dicarbonyl. These compounds have not proven to be among the most effective stabilizers. In general, in this type and in the other types of stabilizers, the presence of an aromatic group does not impart as good stabilizing properties as the presence of an aliphatic, e.g. alkyl, or heterocyclic phosphorus containing group.

Type 3

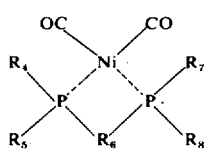

where $R_4$, $R_5$, $R_7$ and $R_8$ are alkyl, aryl, alkaryl or cycloalkyl and $R_6$ is alkylene, preferably of 2 to 3 carbon atoms, e.g. ethylene bis(diphenyl phosphine) nickel⁰ dicarbonyl (hereinafter called Compound 3), trimethylene bis(diphenyl phosphine) nickel dicarbonyl, ethylene bis(dimethylphosphine) nickel dicarbonyl, ethylene bis(diethyl phosphine) nickel dicarbonyl, ethylene bis (diisooctyl phosphine) nickel dicarbonyl, ethylene bis(propyl hexyl phosphine) nickel dicarbonyl, ethylene bis(di-o-tolyphosphine) nickel dicarbonyl, ethylene bis(dicyclohexyl phosphine) nickel dicarbonyl, ethylene bis(dibenzyl phosphine) nickel dicarbonyl, ethylene bis(dioctadecyl phosphine) nickel dicarbonyl, trimethylene bis(debutyl phosphine) nickel dicarbonyl. The compounds wherein $R_4$, $R_5$, $R_7$ and $R_8$ are alkyl have less color than those where these R groups are aryl.

Type 4

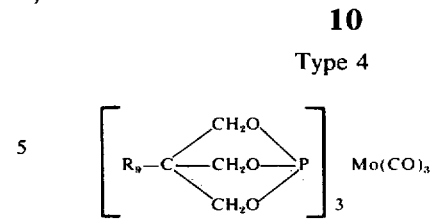

where $R_9$ is a 1 to 17 carbon atom alkyl or is hydroxymethyl, e.g. tris(trimethylol propane phosphite) molybdenum⁰ tricarbonyl (hereinafter called Compound 4), tris(trimethylolethane phosphite) molybdenum tricarbonyl, tris(trimethylolpentane phosphite) molybdenum tricarbonyl, tris(trimethylol heptadecane phosphite) molybdenum (tricarbonyl), tris(pentaerythritol phosphite) molybdenum tricarbonyl. Quite good ultraviolet stabilizing results have been obtained with these compounds. However, they impart some color to the resins which may be objectionable for some uses where the resin must be colorless. These compounds are believed to be novel per se.

Type 5

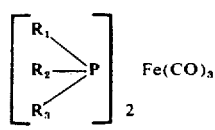

where $R_1$, $R_2$ and $R_3$ are hydrocarbyl as defined above, e.g. bis (triphenyl phosphine) iron⁰ tricarbonyl (hereinafter called Compound 5), bis(trimethyl phosphine) iron tricarbonyl bis(triethyl phosphine) iron tricarbonyl, bis(tripropyl phosphine) iron tricarbonyl, bis(tricyclohexyl phosphine) iron tricarbonyl, bis(tri dodecyl phosphine) iron tricarbonyl, bis(tri[-o-tolyl] phosphine) iron tricarbonyl, bis(tribenzyl phosphine) iron tricarbonyl, bis(tri octadecyl phosphine) iron tricarbonyl. These compounds are not as good stabilizers as the nickel compounds.

Type 6

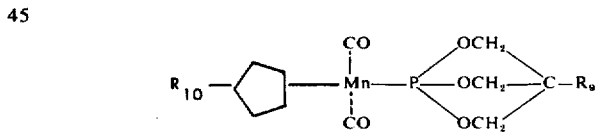

where $R_9$ is as defined above and $R_{10}$ is H or lower alkyl, e.g. methyl cyclopentadienyl manganese dicarbonyl trimethylol propane phosphite (hereinafter called Compound 6), methyl cyclopentadienyl manganese dicarbonyl trimethylol ethane phosphite, methyl cyclopentadienyl manganese dicarbonyl pentaerythritol phosphite, methyl cyclopentadienyl manganese dicarbonyl trimethylol pentane phosphite, methyl cyclopentadienyl manganese dicarbonyl trimethylol heptadecane phosphite, cyclopentadienyl mangnaese dicarbonyl trimethylol propane phosphite, cyclopentadienyl manganese dicarbonyl trimethylol ethane phosphite, cyclopentadienyl manganese dicarbonyl pentaerythritol phosphite, ethyl cyclopentadienyl manganese dicarbonyl trimethylol propane phosphate, propyl cyclopentadienyl manganese dicarbonyl pentaerythritol phosphite. These compounds are new per se.

Type 7

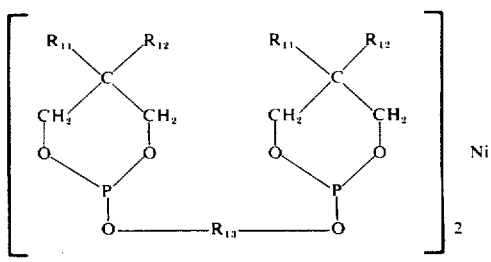

where $R_{11}$ and $R_{12}$ are hydrogen or lower alkyl and $R_{13}$ is lower alkylene of at least 2 carbon atoms or alkylene oxylakylene such as nickel⁰ bis[bis(2,2-dimethyl-1,3-propylene) neopentylene phosphite] (hereinafter called Compound 7) nickel bis[bis(1,3-propylene) trimethylene phosphite], nickel bis[bis(1,3-propylene) neopentylene phosphite], nickel bis[bis(2,2-dimethyl-1,3-propylene) diethylene glycol phosphite], nickel bis[bis(2-methyl-1,3-propylene) 2-methyl propylene phosphite], nickel bis[bis(2,2-diethyl-1,3-propylene) 2,2-diethyl propylene phosphite], nickel bis[bis(2-hexyl-1,3-propylene)-trimethylene glycol phosphite], nickel bis[bis(2-propyl-1,3-propylene)-dipropylene glycol phosphite], nickel bis[bis(2,2-dimethyl-1,3-propylene) dodecamethylene glycol phosphite]. The nickel phosphite complexes of the present invention (both Type 7 and the others as well) unlike most other nickel complexes used as stabilizers do not impair the heat stability of the polypropylene and other polymers. The compounds having the neopentylene group, particularly compound 7, are preferred. The compounds of Type 7 are new per se.

Type 7(a)

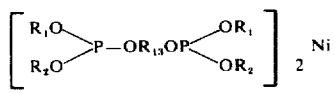

where $R_1$, $R_2$ and $R_{13}$ are as defined above or $R_1$ and $R_2$ are halo lower alkyl where the halogen has an atomic weight of 35 to 80, e.g. nickel⁰bis[ethylene bis(diphenyl phosphite)], nickel bis[neopentylene bis(dilauryl phosphite)], nickel bis[propylene bis(decyl phenyl phosphite)], nickel bis [diethylene glycol bis(diethyl phosphite)], nickel bis (dipropylene glycol bis(didecyl phosphite)], nickel bis [hexylene bis(distearyl phosphite)], nickel bis[trimethylene bis(dieicosanyl phosphite)], nickel bis[1,3-butylene bis(di-p-tolyl phosphite)], nickel bis[neopentylene bis(di-2-chloroethyl phosphite)], nickel bis[ethylene bis(di-2-bromopropyl phosphite)]. The compounds of Type 7(a) are not as stable as those of Type 7 and hence the compounds of Type 7 are preferred thereover.

Type 8

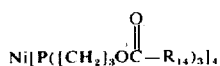

where $R_{14}$ is alkyl of 1 to 3 carbon atoms, e.g. nickel⁰ tetrakis [tris(3-acetoxypropyl phosphine)], hereinafter called Compound 8), nickel tetrakis [tris(3-propionoxypropyl phosphine)], and nickel tetrakis [tris(3-butyroxypropyl phosphine)]. The starting phosphines are prepared by reacting phosphine with allyl acetate, propionate or butyrate. The compounds of Type 8 are new per se.

Type 9

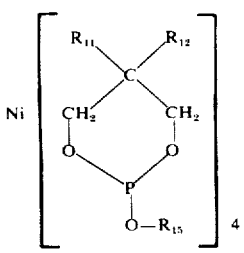

where $R_{11}$ and $R_{12}$ are as defined above and $R_{15}$ is aryl such as nickel⁰ tetrakis (2,2-dimethyl-1,3-propylenephenyl phosphite) (hereinafter called Compound 9), nickel tetrakis (1,3-propylene phenyl phosphite), nickel tetrakis (2-methyl-1,3-propylene phenyl phosphite), nickel tetrakis(2,2-diethyl-1,3-propylene phenyl phosphite), nickel tetrakis (2,2-dimethyl-1,3-propylene p-tolyl phosphite), nickel tetrakis (2,2-dimethyl-1,3-propylene p-nonylphenyl phosphite). The compounds of Type 9 are new per se.

Type 10

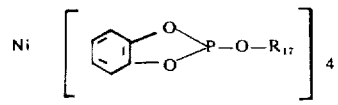

where $R_{17}$ is as $R_1$ or is chloroalkyl, e.g. nickel⁰ tetrakis (o-phenylenephenyl phosphite) (hereinafter called Compound 10), nickel tetrakis (o-phenylene cyclohexyl phosphite) (M.P. 128°-130°C., a white solid decomposing at 230), nickel tetrakis (o-phenylene decyl phosphite), nickel tetrakis (o-phenylene naphthyl phosphite), nickel tetrakis (o-phenylene benzyl phosphite), nickel tetrakis (o-phenylene octadecyl phosphite), nickel tetrakis (o-phenylene methyl phosphite), nickel tetrakis (o-phenylene p-nonylphenyl phosphite), nickel tetrakis (o-phenylene 2-chloroethyl phosphite). The aryl derivatives are not as good as the alkyl, cycloalkyl or chloroalkyl. The cyclohexyl derivative was the best stabilizer of this type. The compounds are new per se.

Type 11

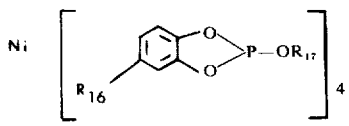

where $R_{17}$ is as defined above and $R_{16}$ is alkyl, e.g. nickel⁰ tetrakis (o-[p-t-butyl]phenylene phenyl phosphite) (hereinafter called Compound 11), nickel tetrakis (o-[p-t-butyl]phenylene decyl phosphite), nickel tetrakis (o-[p-t-amyl]phenylene dodecyl phosphite), nickel tetrakis (o-[p-ethyl]phenylene cyclohexyl phosphite), nickel tetrakis (o-[p-dodecyl]phenylene phenyl phosphite). The compounds are new per se.

Type 11(a)

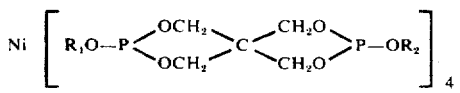

where $R_1$ and $R_2$ are as defined above, e.g. nickel⁰ tetrakis (dilauryl pentaerythritol diphosphite), nickel tetrakis (distearyl pentaerythritol diphosphite), nickel tetrakis (dieicosaryl pentaerythritol diphosphite), nickel tetrakis (diphenyl pentaerythritol diphosphite), nickel tetrakis (dicyclohexyl pentaerythritol diphosphite), nickel tetrakis (didecyl pentaerythritol diphosphite), nickel tetrakis (dibenzyl pentaerythritol diphosphite), nickel tetrakis dicyclohexyl pentaerythritol diphosphite). The compounds are new per se.

Type 11(b)

Nickel⁰ tetrakis (tricyclohexyl phosphine), an off-white solid M.P. 186°–189°C., a new compound prepared in the same way as known nickel hydrocarbyl phosphines of the formula

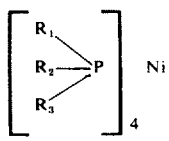

where $R_1$, $R_2$ and $R_3$ are as defined above.

Type 11(c)

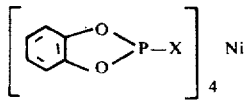

where X is a halogen such as nickel⁰ tetrakis (o-phenylene chlorophosphite) (a white solid, M.P. 165°–169°C., decomposes 170°C.), nickel tetrakis (o-phenylene bromophosphite), nickel tetrakis (o-phenylene iodophosphite). These secondary phosphite complexes showed fair stabilizing activity. They are new per se.

Type 11(d)

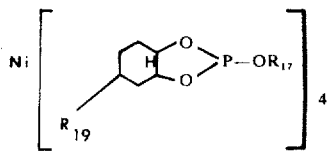

where $R_{17}$ is as defined above and $R_{19}$ is hydrogen or alkyl, such as nickel⁰ tetrakis (o-cyclohexylene phenyl phosphite), nickel tetrakis (o-cyclohexylene cyclohexyl phosphite), nickel tetrakis (o-cyclohexylene lauryl phosphite), nickel tetrakis (o-cyclohexylene benzyl phosphite), nickel tetrakis (o-cyclohexylene 2-chloroethyl phosphite), nickel tetrakis (o-[p-t-butyl]cyclohexylene cyclohexyl phosphite), nickel tetrakis (o-cyclohexylene-2,3-dibromopropyl phosphite), nickel tetrakis (o-[p-ethyl]- cyclohexylene decyl phosphite). The compounds are new per se.

Type 11(e)

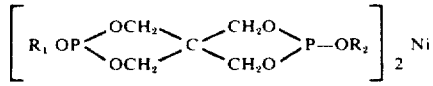

where $R_1$ and $R_2$ are as defined above or haloalkyl, e.g. nickel⁰ bis(distearyl pentaerythritol diphosphite) (M.P. 57–63, a soft waxy solid), nickel bis(di-2-bromopropyl pentaerythritol diphosphite), nickel bis(dilauryl pentaerythritol diphosphite), nickel bis(di-2-chloroethyl pentaerythritol diphosphite), nickel bis(di-2,3-dichloropropyl pentaerythritol diphosphite), nickel bis(diphenyl pentaerythritol diphosphite), nickel bis(-dicyclohexyl pentaerythritol diphosphite). The compounds are new per se.

Type 11(f)

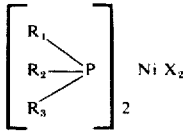

where $R_1$, $R_2$ and $R_3$ are as defined above and X is halogen, e.g. bis (tricyclohexylphosphine) nickel'' dichloride (a pink solid decomposing at 262°C, bis(tricyclohexylphosphine) nickel dibromide, bis(tri lauryl phosphine) nickel dichloride, bis(triphenyl phosphine) nickel dichloride, bis(tribenzyl phosphine) nickel dichloride. This group is ionic type complexes. They are new per se.

Type 12

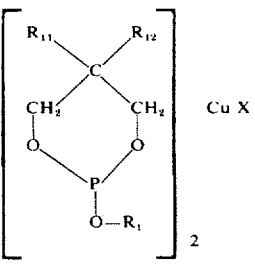

where $R_1$, $R_{11}$ and $R_{12}$ are as defined above and X is halogen, e.g. bis(2,2-dimethyl-1,3-propylene phenyl phosphite) cuprous iodide (hereinafter called Compound 12), bis-(2,2-dimethyl-1,3propylene cyclohexyl phosphite) cuprous iodide, bis(2,2-dimethyl-1,3-propylene lauryl phosphite) cuprous iodide, bis(2,2-dimethyl-1,3-propylene stearyl phosphite) cuprous chloride, bis (2,2-dimethyl-1,3-propylene decyl phosphite) cuprous bromide, bis(1,3-propylene cyclohexyl phosphite) cuprous iodide. This type of compound did not give particularly outstanding results. They are new per se.

Type 12(a)

Nickel⁰ complexes wherein the phosphorus material also contains nitrogen, e.g. nickel⁰ tetrakis (tris[pentamethyleneamine] phosphine)

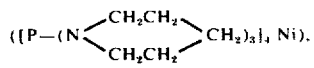

nickel⁰ tetrakis (tris[dimethylaminoethyl] phosphite), nickel tetrakis (tris[diethylaminoethyl] phosphite), nickel tetrakis (tris[dipropylaminopropyl] phosphite), tris (2-[N-dimethylamino] ethyl phosphite) nickel carbonyl (Compound 39), [P(OCH₂CH₂N [CH₃]₂)₃]₃ NiCo, tris (2-[N-diethylamino] propyl phosphite) nickel carbonyl, tetrakis (N-dimethylamino-ethylene phosphite nickel.

Type 13

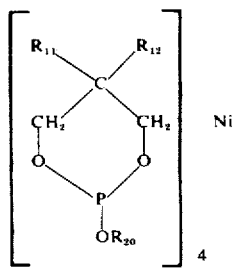

where $R_{11}$ and $R_{12}$ are as defined above and $R_{20}$ is alkyl, aralkyl, cycloalkyl or lower haloalkyl such as nickel⁰ tetrakis (2,2-dimethyl-1,3-propylene cyclohexyl phosphite) (hereinafter called Compound 13), nickel tetrakis (2,2-dimethyl-1,3-propylene lauryl phosphite (a colorless oil), nickel tetrakis (2,2-dimethyl-1,3-propylene stearyl phosphite), nickel tetrakis (2,2-dimethyl-1,3-propylene 2-chloroethyl phosphite), nickel tetrakis (2,2-dimethyl-1,3-propylene methyl phosphite), nickel tetrakis (1,3-propylene cyclohexyl phosphite), nickel tetrakis (2,2-diethyl-1,3-propylene cyclohexyl phosphite), nickel tetrakis (2,2-dimethyl-1,3-propylene 2,3-dibromopropyl phosphite), nickel tetrakis (2-methyl-1,3-propylene isoctyl phosphite), nickel tetrakis (2-propyl-1,3-propylene methyl cyclohexyl phosphite), nickel tetrakis (2-hexyl-1,3-propylene eicosanyl phosphite), nickel tetrakis (2,2-dimethyl-1,3-propylene cyclopentyl phosphite), nickel tetrakis (2,2-dimethyl-1,3-propylene cycloheptyl phosphite), nickel tetrakis (2,2-dimethyl-1,3-propylene benzyl phosphite). The compounds of Type 13 are better stabilizers than those of Type 9. In general, the presence of the alkyl and particularly the cycloalkyl group in the phosphite portion of the molecule gives better results than an aryl group. The compounds are new per se.

Type 14

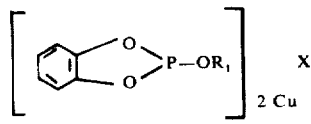

where $R_1$ is as defined above and X is halogen, e.g. bis(o-phenylene phenyl phosphite) cuprous iodide (hereinafter called Compound 14), bis(o-phenylene phenyl phosphite) cuprous chloride, bis(o-phenylene phenyl phosphite) cuprous bromide, bis(o-phenylene methyl phosphite) cuprous chloride, bis(o-phenylene decyl phosphite) cuprous bromide, bis(o-phenylene octadecyl phosphite) cuprous iodide, bis (o-phenylene cyclohexyl phosphite) cuprous iodide), bis (o-phenylene benzyl phosphite) cuprous bromide, bis(o-phenylene m-tolyl phosphite) cuprous chloride. These compounds did not have outstanding activity. The compounds are new per se.

Type 15

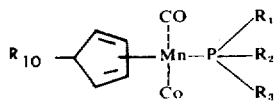

where $R_1$, $R_2$, $R_3$ and $R_{10}$ are as defined above, e.g. methyl cyclopentadienyl manganese dicarbonyl triphenyl phosphine (Compound 15), methyl cyclopentadienyl manganese dicarbonyl tricyclohexyl phosphine, methyl cyclopentadienyl manganese dicarbonyl trimethyl phosphite, methyl cyclopentadienyl managnese dicarbonyl tristearyl phosphine, methyl cyclopentadienyl manganese dicarbonyl didecyl phenyl phosphine, methyl cyclopentadienyl manganese dicarbonyl tribenzyl phosphine, methyl cyclopentadienyl manganese dicarbonyl tri m-tolyl phosphine, cyclopentadienyl manganese dicarbonyl triphenyl phosphine, cyclopentadienyl manganese dicarbonyl trilauryl phosphine, cyclopentadienyl manganese dicarbonyl trieicosanyl phosphine, ethyl cyclopentadienyl manganese dicarbonyl triphenyl phosphine, propyl cyclopentadienyl manganese dicarbonyl triisooctyl phosphine. These compounds show better activity than those of Type 14. They are new per se.

Type 16

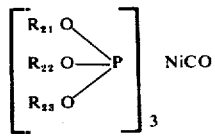

where $R_{21}$, $R_{22}$ and $R_{23}$ are alkyl or aryl or aralkyl or haloalkyl, e.g. tris(triisodecyl phosphite) nickel carbonyl, (hereinafter called Compound 16), tris(trineopentyl phosphite) nickel carbonyl (a new compound which is a white solid M.P. 162°–175°C.) tris(tri-[2-chloroethyl] phosphite) nickel carbonyl, tris(tri-[3-bromo propyl] phosphite) nickel carbonyl, tris(-trimethyl phosphite) nickel carbonyl, tris (octyl didecyl phosphite) nickel carbonyl, tris(ethyl butyl dodecyl phosphite) nickel carbonyl, tris(trioctadecyl phosphite) nickel carbonyl, tris(tri eicosanyl phosphite) nickel carbonyl, tris(tribenzyl phosphite) nickel carbonyl, tris(triphenyl phosphite) nickel carbonyl, tris(-tri-p-nonylphenyl phosphite) nickel carbonyl, tris(-diphenyl decyl phosphite) nickel carbonyl. These compounds showed moderately strong stabilizer activity.

Type 17

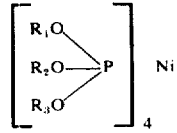

where $R_1$, $R_2$ and $R_3$ are as defined above, e.g. tetrakis(triphenyl phosphite) nickel (hereinafter called Compound 17), tetrakis (tridecyl phosphite) nickel, tetrakis (tricyclohexyl phosphite) nickel, tetrakis(triethyl phosphite) nickel, tetrakis (trioctadecyl phosphite) nickel, tetrakis (tribenzyl phosphite) nickel, tetrakis (tri alpha naphthyl phosphite) nickel. The triaryl compounds of Type 17 had relatively poor stabilizer activity.

Type 18

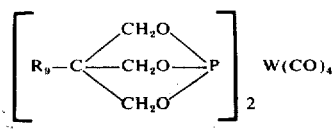

where $R_9$ is as defined above, e.g. bis(trimethylol ethane phosphite) tungsten⁰ tetracarbonyl (hereinafter called Compound 18), bis(trimethylol propane phosphite) tungsten tetracarbonyl, bis(pentaerythritol phosphite) tungsten tetracarbonyl, bis(trimethylol pentane phosphite) tungsten tetracarbonyl, bis(trimethylol heptadecane phosphite) tungsten tetracarbonyl. These compounds are new per se.

Type 19

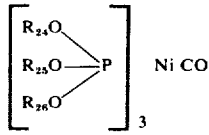

wherein $R_{24}$, $R_{25}$ and $R_{26}$ are cycloalkyl, e.g. tris(tricyclohexyl phosphite) nickel⁰ carbonyl, tris(tri[methylcyclohexyl] phosphite) nickel carbonyl, tris(tricycloheptyl phosphite) nickel carbonyl, tris(tricyclopentyl phosphite) nickel carbonyl. These compounds are new per se. They have outstanding activity. In general, the presence of the cycloalkyl group, particularly cyclohexyl, gives better stabilizing results than were it is replaced by aryl, e.g. phenyl, or alkyl, e.g. decyl. Mixed cycloalkyl, aryl or alkyl phosphite complexes can be used, e.g. tris(dicyclohexyl decyl phosphite) nickel carbonyl, tris(dicyclohexyl phenyl phosphite) nickel carbonyl, tris(cyclohexyl bis[p-nonylphenyl] phosphite) nickel carbonyl, tris(cyclohexyl dilauryl phosphite) nickel carbonyl.

Type 20

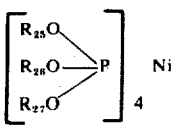

where at least one of $R_{25}$ and $R_{27}$ is halo lower alkyl of at least 2 carbon atoms and the balance of $R_{25}$, $R_{26}$ and $R_{27}$ are halo lower alkyl, alkyl, aryl, cycloalkyl or aralkyl, e.g. tetrakis (tris 2-chloroethyl phosphite) nickel⁰ (hereinafter called Compound 20, M.P. with decomposition 215°C., literature reports 138°-140°C.), tetrakis (tris-2-bromoethyl phosphite) nickel, tetrakis (tris 2-chloropropyl phosphite) nickel, tetrakis (tris 2,3-dichloropropyl phosphite) nickel, tetrakis (tris 3-bromopropyl phosphite) nickel, tetrakis (bis 2-chloroethyl cyclohexyl phosphite) nickel, tetrakis (2-chloroethyl dicyclohexyl phosphite) nickel, tetrakis (bis 2,3-dichloropropyl phenyl phosphite) nickel, tetrakis (bis 2-chloroethyl decyl phosphite) nickel, tetrakis (bis 2-chloroethyl p-nonylphenyl phosphite) nickel, tetrakis (bis 2-bromoethyl benzyl phosphite).

Compound 20 gave outstanding results. It was not as good as the corresponding cyclohexyl compound but was much more economical to produce.

Type 21

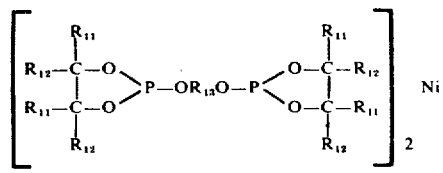

where $R_{11}$, $R_{12}$ and $R_{13}$ are as defined above, e.g. bis(triethylene diphosphite) nickel⁰ (hereinafter called Compound 21), bis(tripropylene diphosphite) nickel, bis(bis[ethylene] diethylene glycol phosphite) nickel, bis(bis[1,2-dibutyl ethylene] hexamethylene phosphite) nickel, bis(bis[1-methyl-2-propyl ethylene] dipropylene glycol phosphite) nickel. These compounds are new and have good stabilizer activity. In general, the higher the amount of nickel and of phosphorus in the heterocyclic compounds such as Types 1, 7, 9, 13, 21, 23 and 26, the better the stabilizer activity. The presence of the cyclohexyl group and the neopentyl group also is advantageous as previously set forth.

Type 22

[(CH₂ = CH CH₂O)₃ P]₄ Ni

This compound is tetrakis (triallyl phosphite) nickel⁰ (hereinafter called Compound 22). It has good stabilizer activity. It appears to be polymeric. Similar results can be obtained with tetrakis (trimethallyl phosphite) nickel. These compounds are novel per se.

Type 23

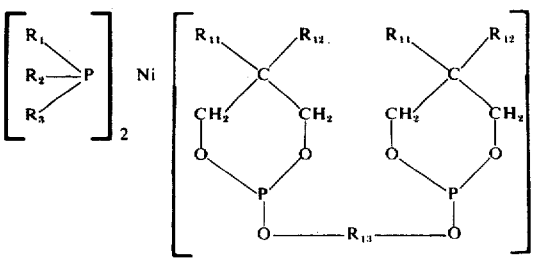

where $R_1$, $R_2$, $R_3$, $R_{11}$, $R_{12}$ and $R_{13}$ are as defined above, e.g. bis(tricyclohexyl phosphine) [bis(2,2-dimethyl-1,3-propylene) neopentylene glycol phosphite] nickel[0] (hereinafter called Compound 23), bis(triphenyl phosphine) [bis (1,3-propylene) ethylene glycol phosphite] nickel, bis (trilauryl phosphine) [bis(2-ethyl-1,3-propylene) hexamethylene glycol phosphite] nickel, bis(-tribenzyl phosphine) [bis(2,2-diethyl 1,3-propylene) diethylene glycol phosphite] nickel, bis(butyl dicyclohexyl phosphine) [bis(2,2-dimethyl-1,3-propylene) neopentylene glycol phosphite] nickel. The compounds are novel per se and have good stabilizer activity. However, phosphines are more expensive than phosphites and do not give compensating better stabilizer activity to justify the increased cost.

Type 24

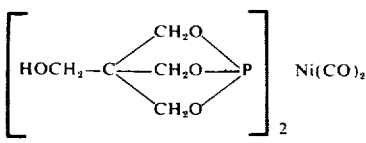

bis(pentaerythritol phosphite) nickel[0] dicarbonyl (hereinafter called Compound 24). This compound is new.

Type 25

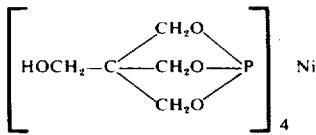

tetrakis(pentaerythritol phosphite) nickel[0] (hereinafter called Compound 25). This compound is new.

Type 26

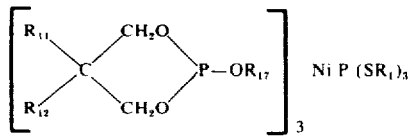

where $R_{11}$, $R_{12}$, $R_{17}$ and $R_1$ are as defined above such as tris(neopentylene glycol phenyl phosphite) trilauryl trithiophosphite nickel[0] (hereinafter called Compound 26), tris(neopentylene glycol cyclohexyl phosphite) trilauryl trithiophosphite nickel, tris(neopentylene glycol lauryl phosphite) trilauryl trithiophosphite nickel, tris(neopentylene glycol cyclohexyl phosphite) tricyclohexyl trithiophosphite nickel, tris(neopentylene glycol 2-chloroethyl phosphite) tricyclohexyl trithiophosphite nickel tris(neopentylene glycol cyclohexyl phosphite) trioctyl trithiophosphite nickel, tris (neopentylene glycol cyclohexyl phosphite) trioctodecyl trithiophosphite nickel, tris(trimethylene glycol methyl phosphite) trieicosanyl trithiophosphite nickel, tris(2-methyltrimethylene glycol cyclohexyl phosphite triphenyl trithiophosphite, nickel, tris(neopentylene glycol benzyl phosphite) tribenzyl trithiophosphite nickel.

The compounds are good stabilizers and those wherein the $R_1$ groups are cyclohexyl are better than those wherein the $R^1$ groups are phenyl. The compounds are new per se.

Type 27

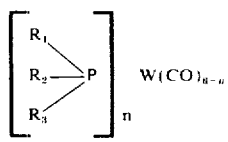

where $R_1$, $R_2$ and $R_3$ are as defined above and $n$ is 2 or 3 such as tris (triphenylphosphine) tungsten[0] tricarbonyl (hereinafter called Compound 27), tetrakis (tributylphosphine) tungsten dicarbonyl (a dark oil), tris (trioctyl phosphine) tungsten tricarbonyl, tis (tricyclohexyl phosphine) tungsten tricarbonyl, tetrakis(-tricyclohexyl phosphine) tungsten dicarbonyl, tris(-trieicosanyl phosphine) tungsten tricarbonyl, tris(tribenzyl phosphine) tungsten tricarbonyl, tris(triethyl phosphine) tungsten tricarbonyl, tetrakis(triphenyl phosphine) tungsten dicarbonyl, tetrakis (tribenzyl phosphine) tungsten dicarbonyl, tetrakis (trioctadecyl phosphine) tungsten dicarbonyl. These compounds are new. They are colored and hence their desirability is reduced where the product should not have such color.

Type 27(a)

There can also be employed the tungsten carbonyl analog of the nickel compounds of Type 9, e.g. bis(2,2-dimethyl-1,3-propylene neopentyl phosphite) tungsten[0] tetracarbonyl, bis (2,2-dimethyl-1,3-propylene decyl phosphite) tungsten tetracarbonyl, bis(1,3-propylene phenyl phosphite) tungsten tetracarbonyl, bis(2-methyl-1,3-propylene benzyl phosphite) tungsten tetracarbonyl, bis 2,2-dimethyl-1,3-propylene cyclohexyl phosphite) tungsten tetracarbonyl, bis(2,2-dimethyl 1-3,-propylene 2-chloroethyl phosphite) tungsten tetracarbonyl.

In preparing compounds of the type $Me(L)_n(A_m)(L')_o$ which contain the $L'$ grouping, e.g. where Me is nickel and L is a phosphite, the simplest procedure is to add the nickel halide to the phosphite in an organic solvent such as alcohol or dioxane. Thus there can be mixed 4 mols of pentaerythritol phosphite with 1 mol of nickel dichloride in alcohol to form tetrakis (pentaerythritol phosphite) nickel dichloride. In similar fashion, 4 mols of trimethylolpropane phosphite with 1 mol of nickel dibromide form tetrakis (trimethylol propane phosphite) nickel dibromide. In like manner, there are formed tetrakis (tricyclohexyl phosphite) nickel dichloride tetrakis (trioctadecyl phosphite) nickel dichloride, tetrakis (triethyl phosphite) nickel dibromide, tetrakis (triphenyl phosphite) nickel dichloride, tetrakis (tribenzyl phosphite) nickel dibromide.

The corresponding nitrates, perchlorates and RCOO— salts can be formed readily by replacing the halogen from the above-identified dihalides by interchange. The perchlorates can also be made directly in a manner analogous to the halides. The organic acid salts can be acetate, propionates, butyrates, benzoates, etc. As previously pointed out, there also can be used known salts such as tetrakis (triphenyl phosphine) nickel dibromide, tetrakis (tricyclohexyl phosphine) nickel dichloride, tetrakis (trioctyl phosphine) nickel dichloride.

Below there are given the methods of preparation for some of the novel compounds and old compounds useful in the invention.

COMPOUND 1

19.5 grams of Ni(CO)$_4$ were added under nitrogen to a flask. Then there were added 18.6 grams of trimethylol propane phosphite in 100 ml. of chlorobenzene. This was stirred until gas evolution ceased. Then there was added 55.8 grams more of trimethylol propane phosphite in 100 ml. of chlorobenzene and the mixture heated to reflux overnight. Then an additional 7 grams of trimethylol propane phosphite were added and the mixture heated at reflux for 6 hours. The mixture was cooled. I.R. analysis showed no metal carbonyl. The product was filtered and the crystalline solid dissolved in hot mother liquor and filtered hot. There was a considerable amount of material precipitated on the filter. The cake was extracted with hot chloroform, filtered and the pale green cake dried.

The filtrate was concentrated until white crystals separated (evaporation was almost to dryness), the solid slurried in hexane, filtered and dried. Both cakes were dried over night.

The first crop was 8.3 grams of a pale green solid and the second crop was 7.9 grams of a white crystalline solid.

The chlorobenzene solution was distilled to remove about 50% of the solvent under reduced pressure from the initial filtrate. A thick white slurry was obtained.

100 ml. of hexane was added. The product was insoluble therein and was recovered by filtering. The white cake was dried in a vacuum oven for about 4 hours to remove all solvent.

Yield 55 grams as a third crop. This third crop was dried in an air oven at 250°F. to remove traces of chlorobenzene. Yield of dried third crop 53.6 grams.

COMPOUND 4

26.4 grams (0.1 mol) of molybdenum hexacarbonyl and 97.2 grams (0.6 mol) of trimethylol propane phosphite were charged to a flask and then 123 grams of chlorobenzene were added and heating was started and continued to reflux at 140°C. Refluxed overnight, the solution was light yellow. Heated for one more hour and then began cooling. A pale yellow precipitate was filtered off and washed with about 20 ml. of fresh chlorobenzene and then twice with 50 ml of hexane. Yield 45.1 grams, M.P. 260 (decomposition). I.R. analysis indicated the compound was Compound 4.

COMPOUND 6

There was added to a flask 21.8 grams (0.1 mol) of methylcyclopentadienyl manganese tricarbonyl, 16.2 grams (0.1 mol) of trimethylol propane phosphite and 100 grams of benzene. At 26°C, the mixture was irradiated with ultraviolet light and stirred overnight (17.5 hours irradiation). The next morning the temperature was 60°C. and the ultraviolet lamp was cut off. The product was again irradiated for 16 hours at about 50°C. and then irradiated for 8 hours. The following day yellow crystals were recovered by filtration. There were obtained 15.57 grams (40% yield) of Compound 6, M.P. (150°–155° flows) 170°–180°C. clear melt. The product was insoluble in water or heptane soluble in acetone and soluble in hot alcohol.

COMPOUND 7

Procedure 1

30 grams (0.075 mol) of bis (2,2-dimethyl-1,3-propylene) neopentylene phosphite were placed in a flask and 6.2 grams (0.036 mol) of nickel tetracarbonyl in 100 ml. of chlorobenzene added. CO was allowed to evolve at room temperature and then the mixture slowly heated up to reflux and held there until 3600 ml. of CO were collected. The mixture was then stripped to 150°C./0.5 mm. to yield a white solid which was recrystallized twice with a 50–50 (by volume) mixture of heptane and benzene. The white solid obtained had a M.P. 255°C., Yield 18 grams.

Procedure 2

The same compound was prepared (M.P. 255°–260°C) by mixing 23 grams (0.0625 mol) of bis (2,2-dimethyl-1,3-propylene) neopentylene phosphite and 5.35 grams (0.0313 mol) of nickel tetracarbonyl in 100 ml. chlorobenzene. The temperature rose to 40°C. during the addition. The mixture was irradiated for 24 hours with ultraviolet light while a dry ice condenser was attached to the flask. Then the mixture was heated to reflux and stripped as in procedure 1 to give the product.

Procedure 3

The same compound was prepared from 72 grams (0.195 mol) of bis (2,2-dimethyl-1,3-propylene) neopentylene phosphite, 150 ml. p-xylene and 16.2 grams (0.095 mol) of Ni(CO)$_4$ in 100 ml. of p-xylene and heating by Method A. The yield was 43.5 grams (80% of theory).

Procedure 4

16.5 grams of tetrakis (trimethyl phosphite) nickel (Compound 36) was treated with 36.8 grams (0.1 mol) of bis (2,2-dimethyl-1,3-propylene) neopentylene phosphite

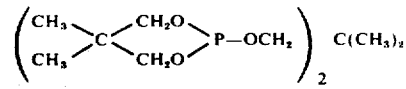

and heated to 150°C./15 mm. 80 ml. xylene was added and distillation resumed, first at room pressure and then in a vacuum. The residue weighed 46.5 grams.

COMPOUND 9

Using Method A, 8.6 grams (0.05 mol) of nickel tetracarbonyl and 150 ml. of chlorobenzene were placed in a flask and 47.5 grams (0.21 mol) of 2,2-dimethyl-1,3-propylene phenyl phosphite were added. The mixture was refluxed for 2.5 hours by which time all the CO (about 4800 ml.) was removed. The mixture was then stripped to 150°C./0.5 mm. to produce a white solid residue which was recrystallized from 80% hexane 20% benzene (by volume) to give a white solid M.P. 166°–170°C., 23 grams, decomposed at 280°C.

The product was obtained in less pure form, M.P. 152°–153°C. by reacting 55.5 grams (0.24×mol) of 2,2-dimethyl-1,3-propylene phenyl phosphite and 10.3 grams (0.06 mol) of Ni(CO)$_4$ and irradiating with ultraviolet light for 24 hours followed by heating at 110°C.

for 7 hours. The product was filtered and recovered as a white solid.

COMPOUND 10

48.5 grams (0.203 mol) of o-phenylene phenyl phosphite, 100 ml. of chlorobenzene and 8.2 grams (0.04775 mol) of Ni(CO)$_4$ were placed in a flask and treated with ultraviolet light for 6.5 hours and then heated at reflux for 48 hours. The solvent was stripped off, 150 ml. of hexane added, the mixture heated to reflux and then cooled and filtered under nitrogen. There were recovered 49.9 grams of Compound 10 as a white crystalline solid, M.P. 110°–116°C.

COMPOUND 11

40 grams of p-t-butylphenylene phenyl phosphite and 50 ml. of chlorobenzene were placed in a flask and 5.2 grams of Ni(CO)$_4$ dissolved in 60 ml. of chlorobenzene were added The mixture was stirred at room temperature for 1 hour, then 16 hours at 110°C. and then at reflux for 6 hours. It was allowed to stand overnight. I.R. analysis showed no carbonyl. The product was stripped to 150/1 mm. leaving Compound 11 as a thick pale tan oily residue. Yield 38.5 grams.

COMPOUND 12

In a flask there were placed 150 ml. of benzene, 9.5 grams (0.05 mol) of cuprous iodide and 22.2 grams (0.10 mol) of phenyl neopentylene phosphite. The mixture was refluxed with stirring for 6 hours, filtered and stripped to yield Compound 12 as a white solid, M.P. 116°–128°C. It was recrystallized from benzene/hexane (40/60 by volume), M.P. 113°–127°C. The benzene/hexane mother liquor from the recrystallization was stripped and there was recovered a white solid, M.P. 120°–136°C.

COMPOUND 13

Procedure 1

150 ml. of p-xylene, 39.0 grams (0.168 mol) of cyclohexyl neopentylene phosphite and 6.5 grams (0.0375 mol) of Ni(CO)$_4$ in 100 ml. of p-xylene were allowed to react for 4 hours at a temperature up to 142°C. until no more CO was evolved. The residue was stripped of solvent. Compound 13 was recovered as a white crystalline material, M.P. 230°–232°C.

Procedure 2

25 grams (0.1075 mol) of cyclohexyl neopentylene phosphite, 4.6 grams (0.0269 mol) of Ni(CO)$_4$ and 150 ml. of chlorobenzene were slowly heated to reflux until no CO was detected. The solvent was stripped off under vacuum. The residue was heated with 100 ml. of methanol, cooled to room temperature and the crystalline solid filtered off. M.P. 230°–232°C with decomposition.

COMPOUND 15

A flask was charged with 39 grams (0.149 mol) of triphenyl phosphine, 33 grams (0.151 mol of methylcyclopentadienyl manganese tricarbonyl and 150 grams of benzene. Irradiation was carried out with ultraviolet light for 50 hours. The solution was filtered, the filtrate was concentrated at reduced pressure to about 100 ml. There was added 200 ml. of hexane. The mixture was allowed to stand overnight and the precipitate filtered off. It was an orange powder, yield 3.6 grams, M.P. 140°–145°C. with decomposition. I.R. analysis showed it was Compound 15.

COMPOUND 19

Procedure 1

150 ml. of p-xylene, 31.5 grams (0.90Xmol) of tricyclohexyl phosphite and 3.6 grams (0.021 mol) of Ni(CO)$_4$ in 100 ml. of p-xylene were placed in a flask and heated to reflux. There were collected 1900 ml. of evolved CO gas (theory 1900 ml.). The solution was cooled to room temperature and then stripped in a vacuum, finally at 40°C./0.05 mm. The residue was 29 grams of a very light green heavy viscous liquid. It had a M.P. of 130°–155°C. after first recrystallization and 165°–190°C. after second recrystallization Ni 5.47% (theory 5.5%).

Procedure 2

150 ml. of chlorobenzene, 83 grams (0.25 mol) of tricyclohexyl phosphite and 10.3 grams (0.06 mol) of nickel tetracarbonyl in 100 ml. of chlorobenzene were allowed to react and the CO evolved collected. There were obtained 1300 ml. at room temperature, 1000 ml. at 26°–70°C., 1500 ml. at 70°–137°C. and 900 ml. upon refluxing for 6 hours at 137°C. or a total of 4700 ml. of CO (theory 5400 ml). The solution was cooled to room temperature and then the solvent stripped off in a vacuum. The residue was a black glass-like solid, weight 93 grams. It was recrystallized from a mixture of 100 ml. acetone and 200 ml. of methyl ethyl ketone by refluxing, adding 2 grams of charcoal at 65°C. and filtering. The filtrate was a clear, dark red solution. It was cooled to room temperature and the solid that precipitated filtered off. The filtrate was reduced to one-half volume and kept in the refrigerator for 4 hours. Crystallization occurred. The first crystals weighed 45.5 grams. The product was recrystallized from 100 ml. of acetone and 220 ml. of methyl ethyl ketone containing 2 grams of charcoal. There were recovered 30 grams of white crystals, M.P. 163°–186°C. which turned brown to black at 180°–186°C.

COMPOUND 20

Procedure 1

134 grams (0.5 mol) of tris 2-chloroethyl phosphite, 150 ml. of p-xylene and 19 grams (0.112 mol) of Ni(CO)$_4$ in 75 ml. of p-xylene were placed in a flask and the CO evolved as follows

| | |
|---|---|
| at 25°C | 3000 ml. |
| at 26–100°C | 5000 ml. |
| at 101–136°C | 1000 ml. |
| at 136–142°C with refluxing for 1 hour | 1000 ml. |

The total CO evolved was 10,000 ml. (theory 10,000 ml.). The solution changed from a clear colorless solution to dark brown and then black at 100°–110°C.

The mixture was heated at reflux four hours, cooled to room temperature and then vacuum stripped, terminal conditions being 145°C./0.1 mm.

The residue in the pot was a heavy black liquid at 100°C. Upon cooling to room temperature, 109.5 grams of a black solid were recovered. It was recrystallized from acetone methanol. There were obtained 42 grams of crystals, M.P. 150°–175°C. to give a dark brown colored liquid with 20% unmelted. It decomposed at 200°C.

Recrystallization from heptane benzene gave 37 grams of product, M.P. 160°–180°C. The chlorine analysis was 37.0% (theory 37.1%).

Procedure 2

67 grams of tris 2-chloroethyl phosphite were mixed with 75 ml. of chlorobenzene and 9.6 grams of Ni(CO)$_4$ in 100 ml. of chlorobenzene added. The CO gas liberated first at room temperature and then by heating to 120°C. amounted to 5,100 ml. The mixture was then stripped of chlorobenzene and residue in the pot analyzed, Cl 36.1%. The melting point was 214°–215°C. 80% melted with discoloration, first turning brown and then black.

COMPOUND 21

100 ml. of chlorobenzene and 56 grams of triethylene diphosphite were placed in a flask and cooled to 5°C. Then there were added 18 grams (0.105 mol) of Ni(CO)$_4$ in 100 ml. of chlorobenzene. The CO gas evolved was collected by the water displacement method. There were collected at a pot temperature of room temperature 3000 ml. CO

| | |
|---|---|
| 30 to 48°C | 1000 ml. |
| 40 to 100°C | 2500 ml. |
| 100 to 133°C | 2500 ml. |

The total CO collected was 9000 ml. (theory 9400 ml.).

The chlorobenzene was stripped from the reaction mixture. The residue in the pot was Compound 21, a light brown crystalline material in an amount of 60 grams. M.P. > 300°C.

COMPOUND 22

There were placed in a flask 100 ml. of chlorobenzene, 8.5 grams (0.05 mol) of nickel tetracarbonyl and 11.0 grams (0.05 mol) of triallyl phosphite. About 1300 ml. of CO came off at room temperature. The solution turned from dark red to very light red. There were then added 11.0 grams (0.05 mol) more of triallyl phosphite and the mixture was stirred. Addition of triallyl phosphite was repeated at room temperature until a total of 0.22 mol had been added. The mixture was then refluxed until the theoretical CO had evolved. The mixture was then stripped to give Compound 22 as a yellow solid, M.P. > 330°C., Yield 40 grams.

The same product was obtained by mixing 44.5 grams (0.22 mol) of triallyl phosphite, 125 ml. of p-xylene and 8.6 grams (0.5 mol) of nickel tetracarbonyl in a solution of 75 ml. of p-xylene all at once, allowing the CO initially released to leave the pot and then refluxing.

COMPOUND 23

8.6 grams (0.05 mol) of nickel tetracarbonyl in 150 ml. of p-xylene was placed in a flask and 28 grams (0.1 mol) of tricyclohexyl phosphine were added at room temperature. The mixture was heated to 50°C and held for 1 hour to form bis (tricyclohexyl phosphine) nickel dicarbonyl. Then at about 30°C., there was added 0.05 mol of bis (2,2-dimethyl-1,3-propylene) neopentylene phosphite and the mixture heated to reflux until no further CO came off. The mixture was stripped at 80°C/0.5 mm. to leave a white residue of 34 grams. This was recrystallized from methanol to give 25 grams of Compound 23, M.P. 275°–277°C., decomposed 325°C.

COMPOUND 24

Pentaerythritol phosphite 6.6 grams (0.035 mols) was melted and dissolved in 250 ml. of p-xylene. There were added 13.2 grams (0.077 mol) of Ni(CO)$_4$ in 100 ml. of p-xylene. Vigorous evolution of CO gas was noted at a temperature which rose to 35°C. The mixture was heated and the CO gas evolved collected at 25° to 142°C. Milky white crystals formed and were separated from the solvent after cooling to room temperature. The solid was stirred and refluxed with 200 ml. of isopropanol for 10 minutes, filtered and dried to give 36 grams of a white solid M.P. >330°C. I.R. analysis showed plus for metal carbonyl.

COMPOUND 25

Procedure 1

125 ml. of 2-butoxyethanol (solvent), 25 grams (0.15 mol) of pentaerythritol phosphite and 5.7 grams (0.034 mol) of Ni(CO)$_4$ in 125 ml. of 2-butoxyethanol were placed in a flask. The CO evolved was collected, initially at room temperature and then with heating to 174°C. until no more CO gas was given off. There were collected 3,350 ml. of CO (theory 3,350). The mixture was cooled to room temperature. The white crystals formed was separated from the solvent and washed with 50 ml. of acetone. The yield of Compound 25 was 18.5 grams (77% of theory). The nickel complex was insoluble in acetone while the starting pentaerythritol phosphite was acetone soluble.

Procedure 2

Compound 25 was also prepared by mixing 20 grams (0.122 mol) of pentaerythritol phosphite, 150 ml. of dibutyl ether and 5 grams (0.03 mol) of Ni(CO)$_4$, slowly heating to reflux and collecting 2950 ml. of CO (theory 2700 ml. CO). The mixture was cooled to room temperature, filtered and the solid washed with hexane, isopropanol, and acetone and dried. Yield 21 grams (theory 21 grams). M.P. >330°C.

Ni 8.50% (theory 8.23%).

Procedure 3

51 grams (0.31 mol) of pentaerythritol phosphite and 250 ml. of dibutyl ether were cooled to 0°C. and 12.5 grams (0.073 mol) of Ni(CO)$_4$ in 50 ml. dibutyl ether were added. The mixture was allowed to react and the CO evolved collected as the temperature was increased to 142°C. The total CO collected was 6500 ml. (theory 6500 ml.). A white solid came out of solution. The mixture was cooled to room temperature and filtered. The solid was washed with 200 ml. of hexane. The solid was stripped to dryness at 80°C./20 mm. for 2 hours and then at 80°C./0.1 mm. for 15 minutes. Yield 50 grams (99%). No melting was noted at 310°C.

COMPOUND 26

200 ml. of chlorobenzene and 8.5 grams (0.05 mol) of Ni(CO)$_4$ were placed in a flask and there were added portionwise 31.7 grams (0.05 mol) of trilauryl trithiophosphite. The mixture was heated up to 60°C. The CO evolved equaled 1000 ml. (theory for 100% evolution is 4500 ml). Then there were added portionwise 34 grams (0.15 mol) of phenyl neopentylene phosphite.

There were evolved 3000 ml. of CO upon heating to 136°C. and maintaning for 0.5 hour. The mixture was cooled to room temperature and left over the weekend. The mixture was then heated to reflux at 136°C. and held for 4 hours. 600 ml. of CO were collected. The total CO collected was 4600 ml.

The solution in the flask was black colored. It was cooled to room temperature and the solvent stripped in a vacuum to a final temperature of 70°C./0.1 mm. The residue was a semi-solid black mass. It was cooled to room temperature and was a semi-solid black mass. The mass was heated to 145°C. in an oil bath.

Next, the residue was dissolved in 150 ml. of heptane and heated to reflux. Then there were added 3 grams of decolorizing charcoal, refluxed for 30 minutes and filtered to give 24 grams of Compound 26 as an off-white (brownish) solid. It was recrystallized from a mixture of 775 ml. of hexane and 25 ml. of benzene to yield 18 grams of an off-white solid, M.P. 157°–158°C., decomposed 170°C.

Ni 4.62%, (theory 4.28%).

COMPOUND 28

(Tetrakis tricyclohexyl phosphine) Nickel

There were placed in a flask 75 ml. of chlorobenzene and 32 grams (0.114 mol) of tricyclohexyl phosphine. To the solution was added 4.8 grams (0.028 mol) of nickel tetracarbonyl in 100 ml. of chlorobenzene. The mixture was refluxed for 4 hours to remove CO (about 2780 ml.). The mixture was then stripped to yield a dark blue solid which was dissolved in chlorobenzene. Toluene was added to precipate Compound 28 as a pale blue solid, M.P. 186°–189°C., Yield 17.1 grams.

COMPOUND 29

Tetrakis (dodecyl neopentylene phosphite) Nickel

There were placed in a flask 44 grams (0.138 mol) of dodecyl neopentylene phosphite (2-dodecoxy-5,5-dimethyl)1,3,2-phosphorinane) and 75 ml. of p-xylene. At room temperature, there were added 5.5 grams (0.032 mol) of Ni(CO)$_4$ in 100 ml. of p-xylene. After refluxing as in Method A, 3050 ml. of CO were removed. The residue after removal of solvent was a colorless oil in an amount of 45.7 grams. It analyzed Ni 4.35% (theory 4.45%).

COMPOUND 30

Bis (2,2-dimethyl-1,3-propylene) Neopentylene Glycol Phosphite Tungsten Tetracarbonyl

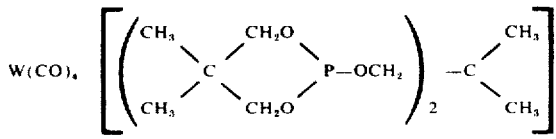

7.04 grams (0.02 mol) of W(CO)$_6$ and 150 ml. of xylene were placed in a flask and 7.4 grams (0.02 mol) of bis (2,2-dimethyl-1,3-propylene) neopentylene glycol phosphite added and the mixture heated to reflux. After 18 hours at reflux, 300 ml. of CO evolved (theory for complete CO removal is 896 ml). The mixture was then irradiated with ultraviolet light, first for 7 hours and then allowed to run another 24 hours. The mixture was stripped and Compound 30 recrystallized from first butanol and then isopropanol as a white solid, M.P. 200°–220°C., decomposed 245°C., Yield 4 grams.

COMPOUND 31

Tris (Tris neopentyl phosphite) Nickel Monocarbonyl 150 ml. of p-xylene, 64.5 grams (0.22 mol) of tris neopentyl phosphite, 8.2 grams (0.047 mol) of Ni(CO)$_4$ in 100 ml. of p-xylene were placed in a flask and the CO released collected, first at room temperature and then by heating the mixture up to 142°C. till no more CO evolved. There were collected 4300 ml. of CO (theory 4250). The solvent was stripped off at reduced pressure. The residue was a white solid. M.P. 155°–172°C., Yield 58.0 grams. It was recrystallized from acetone.

COMPOUND 32

Bis (dioctadecylpentaerythritol diphosphite) Nickel

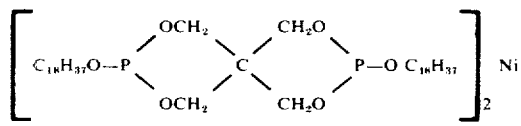

Procedure 1

45 grams (0.062 mol) of dioctadecyl pentaerythritol diphosphite and 200 ml. of chlorobenzene were placed in a flask and 5 grams (0.030 mol) of Ni(CO)$_4$ in 50 ml. of chlorobenzene added. The mixture was slowly heated to reflux until no more gas evolved. 2300 ml. of CO were collected. Five more grams of dioctadecyl pentaerythritol phosphite were added to the reaction mixture which was refluxed for another 1.5 hours. The total CO collected at this point was 2550 ml. Then another 5 grams of the phosphite were added and heating continued for another 1 hour at which time a total of 2700 ml. of CO had evolved. After standing over the weekend, the reaction mixture was stripped, first at the aspirator and then at 0.5 mm. The residue was a yellow oil. It was treated with methanol to yield a white solid, Yield 13 grams, M.P. 55°–66°C.

Procedure 2

There were used 200 ml. of p-xylene, 160 grams (0.22 mol) of distearyl pentaerythritol diphosphite and 17 grams (0.1 mol) of Ni(CO)$_4$ in 100 ml. of xylene. The mixture was heated to reflux over 2 hours and 9500 ml. of CO were collected. The solvent was stripped. The residue was a light brown solid of semi-gel consistency. Yield 155 grams.

COMPOUND 33

Tetrakis (tris[dimethylaminoethyl] phosphite) Nickel 150 ml. of p-xylene, 50 grams (0.17 mol) of tris (dimethylaminoethyl) phosphite were placed in a flask and 6.8 grams (0.04 mol) of Ni(CO)$_4$ in 75 ml. of p-xylene were added dropwise. The CO evolved was collected, 1000 ml. at 25°C., 1000 ml. at 26°–80°C., 1000 ml. at 81°–140°C. and 600 ml. at 141°–142°C. or a total of 3600 ml. (theory 3600 ml.). The mixture was refluxed at 141°C. for 1 hour and then stripped of solvent, eventually in a vacuum at 125°C./0.1 mm. The residue of 49.5 grams was a light brown liquid.

Since I.R. analysis showed some carbonyl, 24 grams of the product was mixed with 26 grams of tris (dimethylaminoethyl) phosphite to form a light brown solution. This was heated to 170°C. for 3 hours and then stripped at 175°C./0.1 mm. to remove the excess tris (dimethylaminoethyl) phosphite. The residue in the pot (Compound 33) was a heavy yellow liquid. Yield 21 grams.

COMPOUND 34

Tris (piperidyl) phosphine tris (phenyl neopentylene phosphite) Nickel 11.5 grams (0.04 mol) of tris (piperidyl) phosphine, 75 ml. of p-xylene and 6.85 grams (0.04 mol) of Ni(CO)$_4$ in 75 ml. of p-xylene were allowed to react at room temperature and the CO evolved was collected in an amount of 950 ml. (theory 900 ml.). Then there were added 30 grams (0.13 mol) of phenyl neopentylene phosphite and the mixture heated to 142°C. There were collected an additional 2850 ml. of CO. The total CO evolved was 3800 ml. (theory 3600 ml.). The solvent was removed by stripping, eventually in a vacuum. The residue was a white solid, yield 45.5 grams. It was recrystallized from hexane to give 20 grams of a white solid, M.P. 137°–168°C.

(The filtrate was dried to yield a further 13 grams of a white solid, M.P. 119°–122°C.)

The 20 grams of solid were recrystallized from hexane to give Compound 34 as a crystalline precipitate, M.P. 155°–162°C. The hexane solution was evaporated to recover additional solids, M.P. 144°–148°C.

COMPOUND 35

Tetrakis (N-diethylamino-ethylene phosphite) Nickel

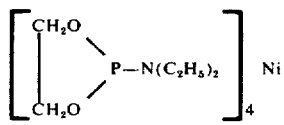

35 grams (0.215 mol) of ethylene diethylamidophosphite and 125 ml. of p-xylene were placed in a flask

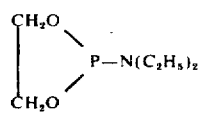

and there were added 8.5 grams (0.05 mol) of Ni(CO)$_4$ in 75 ml. of p-xylene. The mixture was allowed to react, first at room temperature and then up to 142°C. The CO evolved was collected in an amount of 4500 ml. (theory 4480 ml.)

The solution was solvent stripped. Compound 35 was recovered in a yield of 37.5 grams (100% of theory), M.P. 84°–85°C.

COMPOUND 36

Tetrakis(trimethyl phosphite) Nickel[0]

There were placed in a flask 100 ml. of xylene and 37 gms. (0.30 mole) of trimethyl phosphite. To the solution was added 8.6 grams (0.05 mole) of nickel tetracarbonyl in 75 ml. of xylene. The mixture was refluxed for 3 hours to remove the CO. The mixture was stripped at 75°/0.5 mm. There were obtained 40 grams of Compound 36 as a white solid.

COMPOUND 37

Tetrakis(o-phenylene chlorophosphite) Nickel

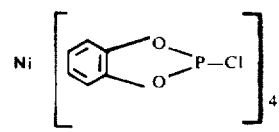

100 ml. of chlorobenzene, 44 grams (0.25 mol) of o-phenylene chlorophosphite and 10.7 grams (0.062 mol) of Ni(CO)$_4$ dissolved in 100 ml. of chlorobenzene were placed in a flask. The CO gas evolved was collected. 2600 ml. was evolved without heating, 1500 ml. was evolved by heating to 50°C. and finally 2700 ml. was evolved by heating for 15 minutes at 135°C. (6,800 ml. total CO was evolved (theory 6,600 ml.). The chlorobenzene was stripped from the reaction product to give Compound 37 as the residue. It was decolorized in conventional manner and had an M.P. of 160°–170°C.

COMPOUND 38

Tetrakis (cyclohexyl o-phenylene phosphite) Nickel

To 26.0 grams (0.109 mol) of o-phenylene cyclohexyl phosphite, there were added 100 ml. of chlorobenzene and 4.0 grams (0.023 mol) of Ni(CO)$_4$ in 100 ml. of chlorobenzene. The CO evolved was collected in an amount of 2500 ml. (theory 2440 ml.). Heating was carried out to reflux at 135°C for ½ hour. The mixture was cooled to room temperature and the chlorobenzene then removed by vacuum stripping. The product had a M.P. of 128°–130°C. and decomposed at 230°C., Ni 5.3% (theory 5.8%).

Table 1

| Compound Number | Method of Preparation | Appearance | Melting Point °C | Percent Metal |
|---|---|---|---|---|
| 1 | A | white solid | 270° (some dec) | 8.3% Ni |
| 2 | A | lt yellow crystalline solid | 200° dec. | 8.2% Ni |
| 3 | A | lt yellow solid | 137–140° | 11.5% Ni |
| 4 | A | off-white solid | 260° (dec.) | 14.5% Mo |
| 5 | A | yellow solid | 270° dec. | 8.4% Fe |
| 6 | A | yellow solid | 170–180° | 15.6% Mn |
| 7 | A | white solid | 255–260° | 7.4% Ni |
| 8 | A | green solid | dec. 164° | 12.1% Ni |
| 9 | A | white solid | 151–157° | 5.8% Ni |
| 10 | A | white crystalline solid | 110–116° | 5.8% Ni |
| 11 | A | pale tan glass | — | 4.85% Ni |
| 12 | D | white solid | 105–110° | 9.8% Cu |
| 13 | A | white solid | 230–232° dec. | 6.0% Ni |
| 14 | D | white solid | 120–125° | 9.7% Cu |
| 15 | A | yellow solid | 112° | 12.2% Mn |
| 16 | A | amber liquid | — | 3.7% Ni |
| 17 | A | sl yellow solid | 107° | 4.5% Ni |
| 18 | A | white solid | dec. 245° | 27.6% W |
| 19 | A | white solid | 166–170° | 5.5% Ni |
| 20 | A | white solid | 215° dec. | 5.2% Ni |
| 21 | A | yellow solid | 300° | 10.8% Ni |
| 22 | A | pale yellow solid | 330° | 6.8% Ni |
| 23 | A | white solid | 275–277° | 6.3% Ni |
| 24 | A | white solid | 330° | 13.3% Ni |
| 25 | A | white solid | 330° | 8.2% Ni |
| 26 | A | off-white solid | 157–158° | 4.7% Ni |
| 27 | A | yellow solid | 260° dec. | 19.2% W |
| 29 | A | colorless liquid | — | 4.4% Ni |
| 31 | A | white solid | 162–175° | 6.1% Ni |
| 34 | A | white solid | 158–162° | 5.7% Ni |
| 35 | A | off-white solid | 84–85° | 8.3% Ni |

Table 1-continued

| Compound Number | Method of Preparation | Appearance | Melting Point °C | Percent Metal |
|---|---|---|---|---|
| 39 | A | yellow glass | — | 6.0% Ni |

In addition to their stabilizing properties, the compounds of the present invention also are good flame proofing agents due to their phosphorus content. Thus they can be used as flame proofing agents with the polymers and in the manner disclosed by Grayson U.S. Pat. No. 3,294,870, Dec. 27, 1966, col. 4, line 3 to col. 5, line 28.

While the compounds of the present invention are useful in the manner of conventional heat and light stabilizers, e.g. with vinyl chloride resins, they are primarily useful as ultraviolet light stabilizers, probably because they are triplet quenchers. They also are useful as dye assistant as they provide "dyesites" in the polymer formulations.

While the ultraviolet light stabilizers of the present invention are most useful as ultraviolet light stabilizers for polypropylene and propylene copolymers with other hydrocarbons, their utility is not limited thereto.

The ultraviolet light stabilizers of the present invention are particularly effective with solid polyethylene, polypropylene, ethylene propylene copolymers (e.g. 50:50, 80:20 and 20:80), ethylene-monoolefin copolymers wherein the monoolefin has 4–10 carbon atoms and is present in a minor amount, e.g. ethylene-butene-1 copolymer (95:5) and ethylenedecene-1 copolymer (90:10). Furthermore, they can be used to stabilize natural rubber, styrene-butadiene rubber (SBR rubber), e.g. (75% butadiene-25% styrene), EPDM rubbers, ABS terpolymers (e.g. 20-30% acrylonitrile, 20–30% butadiene, 40–60% styrene), polyisoprene, polybutadiene, styrene-acrylonitrile copolymers butyl rubber, polyacrylonitrile and acrylonitrile copolymers (e.g. acrylonitrile-vinyl chloride 85:15), polystyrene, impact modified polystyrene, butadieneacrylonitrile (e.g. 60:40); polymerized acrylates and methacrylate, e.g. polymethyl acrylate polymethyl methacrylates and polybutyl acrylate, polyacetals, e.g. polyoxymethylene polymers (e.g. Delrin and Celcon), polycarbonates (e.g. bisphenol A-carbonate polymer), polysulfones, polyphenyleneoxides, phenoxy resins, epoxy resins, A-epichlorhydrin, nylon, cellulose acetate, cellulose acetatepropionate cellulose acetate-butyrate, cellulose nitrate, ethyl cellulose, linear polyesters, e.g. polyethylene terephthalate (Dacron, Mylar), unsaturated polyesters, e.g. vinyl compounds modified alkyds such as ethylene glycol phthalate-maleate modified with styrene or diallyl phthalate, oil modified alkyd resins, e.g. soybean oilglyceryl phthalate resin, chlorosulfonated polyethylene, polyurethanes (e.g. toluene diisocyanate reaction products with polypropylene glycol molecular weight 2025 or with glycerine-ethylene oxide adduct having a hydroxyl number of 56)

As the EPDM rubber there can be employed many of the commercially available EPDM rubbers. The EPDM rubber normally contains 30 to 70 molar percent (preferably 50 to 60 molar percent) of ethylene, 65 to 20 molar percent (preferably 35 to 45 molar percent propylene) and 1 to 15 molar percent (preferably 3 to 5 molar percent) of the nonconjugated polyolefin. Usually the polyolefin is not over 10 molar percent. The ethylene and propylene can each be 5 to 95 molar percent of the composition.

As used in the present specification and claims, the term nonconjugated polyolefin includes aliphatic nonconjugated polyene hydrocarbons and cycloaliphatic nonconjugated polyene hydrocarbons, e.g. endocyclic dienes. Specific examples of suitable nonconjugated polyolefins include pentadiene-1,4; hexadiene-dicyclopentadiene, methyl cyclopentadiene dimer, cyclododecatriene, cyclooctadiene-1,5; 5-methylene-2-norbornene.

Specific examples of suitable terpolymers are the Royalenes which contain 55 mole percent ethylene, 40 to 42 mole percent propylene and 3 to 5 mole percent dicyclopentadiene; Enjay terpolymers, e.g., ERP-404 of Enjay and Enjay 3509 which contains about 55 mole percent ethylene, 41 mole percent propylene and 4 mole percent 5-methylene-2-norbornene; Nordel, a terpolymer of 55 mole percent ethylene, 40 mole percent propylene and 5 mole percent hexadiene-1,4. Another suitable terpolymer is the one containing 50 mole percent ethylene, 47 mole percent propylene and 3 mole percent 1,5-cyclooctadiene (Dutrel).

Examples of EPDM rubbers are given in U.S. Pat. Nos. 2,933,480; 3,000,866; 3,063,973; 3,093,620; 3,093,621, and 3,136,739, in British Pat. No. 880,904 and in Belgian Pat. No. 623,698.

The ultraviolet light stabilizer compositions of the present invention are also useful with other solid polymers. Thus they can be used with resins made from vinylidene compounds such as vinyl chloride, vinylidene chloride, vinyl chloroacetate, chlorostyrenes, vinyl bromide and chlorobutadienes.

Such vinylidene compounds may be polymerized alone or in admixture with each other or with vinylidene compounds free from halogen. Among the halogen free materials which can be copolymerized with the halogen containing vinylidene compounds, e.g. vinyl chloride, are vinyl esters of carboxylic acids, e.g. vinyl acetate, vinyl propionate, vinyl butyrate and vinyl benzoate, esters of unsaturated acids, e.g., alkyl and alkenyl acrylates such as methyl acrylate, ethyl acrylate, propyl acrylate, butyl acrylate and allyl acrylate as well as the corresponding methacrylates, e.g. methyl methacrylate and butyl methacrylate, vinyl aromatic compounds, e.g. styrene, p-ethyl styrene, divinyl benzene, vinyl naphthalene, alpha-methyl styrene, p-methyl styrene, dienes such as butadiene and isoprene, unsaturated amides such as acrylamide, methacrylamide and acrylanilide and the esters of alpha, beta-unsaturated carboxylic acids, e.g. The methyl, ethyl, propyl, butyl, amyl, hexyl, heptyl, octyl, allyl, methallyl and phenyl esters of maleic, crotonic, itaconic and fumaric acids and the like. Specific examples of such esters are diethyl maleate, dibutyl fumarate.

The copolymers in which at least 50% of the copolymer is made from a halogen containing vinylidene compound such as vinyl chloride are frequently treated according to the invention.

The stabilizers of the present invention are also effective when intimately mixed with halogen containing resins in which part or all of the halogen is introduced into a preformed resin, e.g. chlorinated polyvinyl acetate, chlorinated polystyrene, chlorinated polyethylene, chlorinated polyvinyl chloride, chlorinated natural and synthetic rubbers and rubber hydrochloride.

Typical examples of copolymers include vinyl chloride vinyl acetate (95:5 weight ratio), vinyl chloride vinyl acetate (87:13 weight ratio), vinyl chloride-vinyl acetate-maleic anhydride (86:13:1 weight ratio), vinyl chloride-vinylidene chloride (95:5 weight ratio), vinyl chloride-diethyl fumarate (95:5 weight ratio), vinyl chloride-trichloroethylene (95:5 weight ratio).

The resin, e.g. polyvinyl chloride, can either be plasticized or unplasticized. As the plasticizer there can be employed conventional materials such as dioctyl phthalate, octyl decyl phthalate, tricresyl phosphate, 2-ethylhexyl diphenyl phosphate, dodecyl dicresyl phosphate, tributyl acetyl citrate, dioctyl sebacate, dibutyl sebacate, etc. The plasticizer is used in conventional amount, e.g. 10 to 150 parts for each 100 parts of the vinyl chloride containing resin.

There can also be incorporated 0.1 to 10 parts per 100 parts of the halogen containing resin of a metal salt stabilizer. Thus, there can be used barium, strontium, calcium, cadmium, zinc, lead, tin, magnesium, cobalt, nickel, titanium and aluminum salts of phenols, aromatic carboxylic acids, fatty acids and epoxy fatty acids.

Examples of suitable salts include barium di(nonylphenolate), strontium di(nonylphenolate), strontium di(amylphenolate), barium di(octylphenolate), strontium di(octylphenolate), barium di(nonyl-o-cresolate), lead di(octylphenolate), cadmium-2-ethylhexoate, cadmium laurate, cadmium stearate, zinc caprylate, cadmium caproate, barium stearate, barium 2-ethylhexoate, barium laurate, barium ricinoleate, lead stearate, aluminum stearate, magnesium stearate, calcium octoate, calcium stearate, cadmium naphthenate, cadmium benzoate, cadmium p-tert, butylbenzoate, barium octyl salicylate, cadmium epoxy stearate, strontium epoxy stearate, cadmium salt of epoxidized acids of soybean oil, and lead epoxy stearate.

In plastisol formulations there is preferably also included from 0.1 to 10 parts per 100 parts of resin of an epoxy vegetable oil such as epoxidized soybean oil or epoxidized tall oil.

There can also be incorporated conventional phosphites in an amount of 0.1 to 10 parts per 1000 parts of polymer. Typical of such phosphites are triphenyl phosphite, tris decyl phosphite, decyl diphenyl phosphite, di(p-t-butylphenyl) phenyl phosphite, di-phenyl-o-cresyl phosphite, trioctyl phosphite, tricresyl phosphite, tribenzyl phosphite, polymeric phosphites such as Weston 243-B (made in accordance with U.S. Pat. No. 3,341,629) and prepared from triphenyl phosphite and hydrogenated bisphenol and having a molecular weight of about 3000 and Weston 440 (a linear polymeric pentaerythritol hydrogenated bisphenol A phosphite made in accordance with U.S. Pat. No. 3,053,878, distearyl pentaerythritol diphosphite, thiophosphites such as trilauryl trithiophosphite, trioleyl trithiophosphite and tristearyl trithiophosphite.

There can also be included thio compounds conventionally employed in monoolefin polymers formulations, e.g. in an amount of 0.01 to 10%, usually 0.1 to 5% of the polymer. Thus, there can be used pentaerythritol tetra (mercaptoacetate), 1,1,1-trimethylolethane tri (mercaptoacetate), 1,1,1-trimethylolpropane tri (mercaptoacetate), dioleyl thiodipropionate, dilauryl thiodipropionate, other thio compounds include distearyl 3,3'-thiodipropionate, dicyclohexyl-3,3'-thiodipropionate, dicetyl-3,3'-thiodipropionate, dioctyl-3,3'-thiodipropionate, dibenzyl-3,3'-thiodipropionate, lauryl myrietyl-3,3'-thiodipropionate, diphenyl-3,3'-thiodipropionate, di-p-methoxyphenyl-3,3'-thiodipropionate, didecyl-3,3'-thiodipropionate, dibenzyl-3,3'-thiodipropionate, diethyl-3,3'-thiodipropionate, lauryl ester of 3-methyl-mercapto propionic acid, lauryl ester of 3-butyl-mercapto propionic acid, lauryl ester of 3-laurylmercapto propionic acid, phenyl ester of 3-octylmercapto propionic acid, lauryl ester of 3-phenylmercapto propionic acid, lauryl ester of 3-benzyl-mercapto propionic acid, lauryl ester of 3-(p-methoxy) phenylmercapto propionic acid, lauryl ester of 3-cyclohexyl-mercapto propionic acid, lauryl ester of 3-hydroxymethylmercaptopropionic acid, myristyl ester of 3-hydroxyethylmercapto propionic acid, octyl ester of 3-methoxymethylmercapto propionic acid, dilauryl ester of 3-carboxylmethylmercapto propionic acid, diluaryl ester of 3-carboxypropylmercapto propionic acid, diluaryl-4,7-dithiasebacate, dilauryl-4,7,8,11-tetrathiotetradecandioate, dimyristyl-4,11-dithiatetradecandioate, lauryl-3-benzothiazylmercaptopropionate. Preferably the esterifying alcohol is an alkanol having 10 to 18 carbon atoms. Other esters of beta thiocarboxylic acids set forth in Gribbins U.S. Pat. No. 2,519,744 can also be used.

Likewise, there can be included 0.01 – 10%, usually 0.1 – 5% in the monoolefin polymer formulations polyvalent metal salts. Examples of such salts are calcium stearate, calcium 2-ethylhexoate, calcium octate, calcium oleate, calcium ricinoleate, calcium myristate, calcium palmitate, calcium laurate, barium laurate, barium stearate, magnesium stearate, as well as zinc stearate, cadmium laurate, cadmium octoate, cadmium stearate and the other polyvalent metal salts of fatty acids set forth previously.

There can also be added phenolic antioxidants in an amount of 0.01–10%, preferably 0.1–5%. Examples of such phenols include 2,6-di-t-butyl-p-cresol (Ionol), butylated hydroxyanisole, propyl gallate, 4,4'-thiobis(6-t-butyl-m-cresol), 4,4'-cyclohexylidene diphenol, 2,5-di-t-amyl hydroquinone, 4,4'-butylidene bis(6-t-butyl-m-cresol), hydroquinone monobenzyl ether, 2,2'-methylene-bis(4-methyl-6-t-butylphenol) (Catalin 14), 2,6-butyl-4-decyloxyphenol, 2-t-butyl-4-dodecyloxyphenol, 2-t-butyl-4-dodecyloxyphenol, 2-t-butyl-4-octadecyloxyphenol, 4,4'-methylene-bis(2,6-di-t-butyl phenol), p-aminophenol, N-lauryloxy-p-aminophenol, 4,4'-thiobis(3-methyl-6-t-butylphenol), bis[o-(1,1,3,3-tetramethylbutyl) phenol] sulfide, 4-acetyl-beta-resorcylic acid, A stage p-t-butylphenolformaldehyde resin, crotonaldehyde condensate of 3-methyl-6-t-butyl-phenol, 2,6-di-t-butyl, p-cresol (Toponol CA), 2,2-methylene bis 4-ethyl-6-t-butylphenol (AO-425), 4-dodecyloxy-2-hydroxy-benzophenone, 3-hydroxy-4-(phenylcarbonyl) phenyl palmitate, n-dodecyl ester of 3-hydroxy-4-phenylcarbonyl) phenoxyacetic acid, and t-butylphenol.

The use of epoxy compounds in an amount of 0.01–5% in the monoolefin and other polymer compositions is also valuable. Examples of such epoxy compounds include epoxidized soya bean oil, epoxidized lard oil, epoxidized olive oil, epoxidized linseed oil, epoxidized castor oil, epoxidized peanut oil, epoxidized corn oil, epoxidized tung oil, epoxidized cottonseed oil, epichlorhydrinbisphenol A resins (epichlorhydrindiphenylolpropane resins), phenoxy-propylene oxide, butoxypropylene oxide, epoxidized neopentylene oleate, glycidyl epoxystearate, epoxidized alpha-olefins, epoxidized glycidyl soyate, dicyclopentadiene dioxide; epoxidized butyl tallate, styrene oxide, dipentene dioxide, glycidol, vinyl cyclohexene dioxide, glycidyl ether of resorcinol, glycidol ether of 1,5-dihydroxynaphthalene, epoxidized linseed oil fatty acids, allyl glycidyl ether, butyl glycidyl ether, cyclohexane oxide, 4-(2,3-epoxypropoxy) acetophenone, mesityl oxide epoxide, 2-ethyl-3-propyl glycidamide, glycidyl ethers of glycerine, pentaerythritol and sorbitol, and 3,4-epoxycyclohexane-1,1-dimethanol bis-9,10-epoxystearate.

The novel ultraviolet light stabilizers of the present invention are generally used in an amount of 0.005 to 10 (or even 20 parts) per 100 parts of polymer to be stabilized. Preferably, they are employed in an amount of 0.1 to 5 parts per 100 parts of polymer.

Frequently it is desirable to incorporate conventional ultraviolet light absorbers, e.g. in an amount of 0.005 to 10 parts, preferably 0.1 to 5 parts, per 100 parts of polymer. In many cases, synergistic effects have been noted.

Examples of such ultraviolet light absorbers include benzophenones such as 2-hydroxy-4-methoxybenzophenone, 2,4-dihydroxy-benzophenone, 2,2′-dihydroxy-4-methoxy-benzophenone, 2,2°-dihydroxy-4-n-octoxy-benzophenone, 2-hydroxy-4-n-octoxybenzophenone (Cyasorb 531), 2-hydroxy-4-butoxybenzophenone, 4′-chloro-2-hydroxy-4-octoxybenzophenone, 5-chlor-2-hydroxy-benzophenone, 2,4-dibenzoyl resorcinol, 4-dodecyloxy-2-hydroxybenzophenone, 2,2′-dihydroxy, 4,4′-dimethoxybenzophenone, 2,2′,4,4′,-tetrahydroxybenzophenone, 2-hydroxy-4-methoxybenzophenone-5-sulfonic acid, sodium 2,2′-dihydroxy-4,4′ dimethoxy-5-sulfobenzophenone, 2,2′-dihydroxy-4-butoxybenzophenone, 2,2′-dihydroxy-4-dodecoxybenzophenone, 2-hydroxy-4-octadecoxybenzophenone, 2,2′-dihydroxy-4,4-ethoxy benzophenone, 2,2′-dihydroxy-4-heptadecoxy-benzophenone, 2-hydroxy-4-n-heptadecoxybenzophenone, 2-hydroxy-4-methoxy-2′-carboxybenzophenone 2-hydroxy-4-(2-hydroxy-3-methylacryloxy) propoxy benzophenone, 2-hydroxy-4-methoxy-4′-methyl benzophenone, salicylates such as phenyl salicylate, 4-t-butylphenyl salicylate, 4-octyl-phenyl salicylate, bisphenol A disalicylate, carboxyphenyl salicylate, strontium salicylate, methyl salicylate, dodecyl salicylate, resorcylates such as resorcinol monobenzoate, benzylidene malonates such as diethyl p-methoxybenzylidene malonate, dimethyl-p-methoxybenzylidene malonate, diethyl o-methoxybenzylidene malonate, diethyl p-hydroxybenzylidene malonate, benzotriazoles such as 2-hydroxy-phenylbenzotriazole and alkyl substituted derivatives thereof, 2(2′-hydroxy-5′-methyl phenyl) benzotriazole Tinuvin P), 2-cyanostilbyl-4-naphthotriazole, 2(-2-hydroxy-5-ethyl phenyl) benzotriazole, 2(-2-hydroxy-5-octyl phenyl) benzotriazole, Tinuvin 328 (a substituted benzotriazole), 2(2′-hydroxy-3′,5′-di-t-butylphenyl) triazole (Tinuvin 327), 2(2′-hydroxy-3′-di-t-butyl-5′-methylphenyl) benzotriazole (Tinuvin 326), 2-(2′-hydroxy-4′-methoxyphenyl) benzotriazole, 2-(2′-hydroxy-3′,5′-di-t-amylphenyl) benzotriazole, 2-(2′-hydroxy-3′,5′-di-t-butylphenyl(-5-chlorobenzotriazole, substituted acrylonitriles of the formula

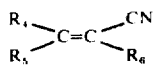

where $R_4$ and $R_5$ are alkyl or aryl and $R_6$ is an electronegative substituent such as ethyl 2-cyano-3,3′diphenyl acrylate, 2-ethylhexyl-2-cyano-3,3-diphenyl acrylate, alpha-phenylbenzylidene-malononitrile, diphenylbenzylidene-malononitrile, conventional metal (particularly nickel) organic complexes such as Ferro AM 101 (nickel complex of the formula

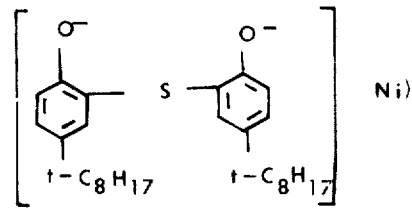

Cyasorb UV 1084 (nickel complex of the formula

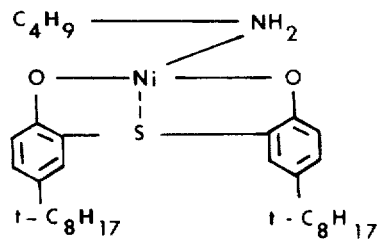

also called 2,2′-thiobis-(4-t-octylphenolate) n-butylamine nickel), nickel bis(octylphenyl sulfide).

There can also be used triazines such as those having at least one o-hydroxyphenyl substituent such as 2,4,6-tris-(2-hydroxy-4-octyloxy-phenyl)-s-triazine, 2-(2-hydroxy-4-octyloxyphenyl)-4,6-dixylyl-s-triazine, benzothiazoles such as 2-anilinobenzo thiazole, 2-(N-methylanilino) benzothiazole, 2-(4-methoxyanilino) benzothiazole, 2-(2-methoxylphenylimino) 3-ethylbenzothiazoline, 2-phenylimino-3-ethylbenzothiazoline and 2-(beta-naphthylimino) benzothiazoline, arylaminoethylenes such as N-methyl p-methoxyanilinomethylenemalonitriles, diphenylaminomethylenemalononitrile, N-methyl-p-methoxyanilinomethylmalononitrile, guanidines such as 1,2-dibenzoyl-3-arylguanidines, e.g. 1,2-dibenzoyl-3-(p-methoxyphenyl) guanidine; 1,2-dibenzoyl-3-(p-chlorophenyl) guamidine, 1,2-di(p-methoxybenzoyl)-3-(p-methoxyphenyl) guanidine.

There can be used any of the ultraviolet light absorbers disclosed in Di Giaimo U.S. Pat. No. 3,496,134 issued Feb. 17, 1970, or any of the patents referred to therein on col. 3, lines 40 to col. 4, line 33. The entire disclosure of Di Giaimo and of all the patents cited therein, namely, U.S. Pat. Nos. 2,777,838; 2,682,559; 2,693,492; 2,861,053; 2,919,259; 2,976,259; 3,006,959; 3,098,842; 3,004,896; 3,108,269; 3,271,339; 3,146,217; 3,118,887; 3,293,247; 3,293,249; 3,244,668; 3,079,336; 3,074,971; 3,085,097; 3,111,417; 3,149,146; 3,215,724 and 3,278,448 is hereby incorporated by reference.

The formulations in Table 2 below all contained 100 parts of solid polypropylene, 0.3 parts of distearyl thiodipropionate, 0.1 part of Irganox 1010 (pentaerythritol tetrakis[3(3,5-di-t-butyl-4-hydroxyphenyl)]) propionate and the indicated amounts of the other indicated materials. The formulations were all made up as 50 mil films and used as test strips in the Atlas Weather-O-Meter. The abbreviation pph indicates "parts per hundred parts of polymer". Control A had 0.25 pph of 2-hydroxy-4-octoxy-benzophenone and Control B had no other additive.

Table 2

| Compound Number | Metal Complex (pph) | 2-Hydroxy-4-Octoxy-benzo-phenone, (pph) | Color Initial | Color Final | Hours to Failure |
|---|---|---|---|---|---|
| Control A | — | 0.25 | colorless | colorless | 200 |
| Control B | — | — | colorless | colorless | 100 |
| 5 | 0.5 | — | lt. yellow | same | 150 |
| 4 | 0.5 | — | blue | blue | 300 |
| 6 | 0.5 | — | lt. yellow | lt. yellow | 200 |
| 15 | 0.5 | — | lt. yellow | lt. yellow | 250 |
| 7 | 0.5 | — | colorless | colorless | 380 |
|  | 0.25 | 0.25 | colorless | colorless | 640 |
| 20 | 0.5 | — | colorless | colorless | 300 |
|  | 0.25 | 0.25 | colorless | colorless | 400 |
| 23 | 0.40 | 0.25 | lt. green | lt. green | 800 |
|  | 0.81 | — | colorless | colorless | 600 |
| 22 | 0.38 | 0.25 | colorless | colorless | 800 |
|  | 0.76 | — | sl. yellow | colorless | 500 |
| 24 | 0.195 | 0.25 | colorless | colorless | 600 |
|  | 0.39 | — | colorless | colorless | 400 |
| 25 | 0.315 | 0.25 | colorless | colorless | 800 |
|  | 0.630 | — | colorless | colorless | 500 |
| 21 | 0.25 | 0.25 | colorless | colorless | 500 |
| 27 | 0.27 | — | off-white | tan | 200 |
| 19 | 0.5 | — | colorless | colorless | 400 |
|  | 0.25 | 0.25 | colorless | colorless | 900 |
| 9 | 0.5 | — | colorless | colorless | 440 |
|  | 0.25 | 0.25 | colorless | colorless | 540 |
| 13 | 0.5 | — | colorless | colorless | 440 |
|  | 0.25 | 0.25 | colorless | colorless | 540 |
| 16 | 0.5 | — | colorless | colorless | 360 |
|  | 0.25 | 0.25 | colorless | colorless | 400 |
| 26 | 0.5 | — | colorless | (still on test) |  |
|  | 0.25 | 0.25 | colorless | (still on test) |  |
| 35 | 0.5 | — | colorless | (still on test) |  |
|  | 0.25 | 0.25 | colorless | (still on test) |  |
| 34 | 0.5 | — | colorless | (still on test) |  |
|  | 0.25 | 0.25 | yellow | (still on test) |  |
| 29 | 0.5 | — | colorless | colorless | 300 |
|  | 0.25 | 0.25 | colorless | colorless | 600 |
| 31 | 0.5 | — | yellow | (still on test) |  |
|  | 0.25 | 0.25 | yellow | (still on test) |  |
| 32 | 0.5 | — | colorless | (still on test) |  |
|  | 0.25 | 0.25 | yellow | (still on test) |  |

In place of the compounds of the present invention used in Table 2, there can be employed in the same formulation in place thereof and in the same amount, any of the other metal-trivalent phosphorus complexes disclosed as useful in the present invention. Likewise, in place of polypropylene in Table 2 with the ultraviolet light stabilizers of the present invention, there can be employed any of the other polymers set forth supra.

Additional illustrative formulations include the following:

Formulation 1

| Profax 6501 (an unstabilized polypropylene) | 100 parts |
|---|---|
| Calcium stearate | 0.1 part |
| Irganox 1010 | 0.1 part |
| Compound 26 | 0.5 part |
| Distearyl thiodipropionate | 0.3 part |

Formulation 2

| Polypropylene (Profax 6501) | 100 parts |
|---|---|
| Compound 23 | 1 part |

Formulation 3

| Profax 6501 | 100 parts |
|---|---|
| Dioleyl thiodipropionate | 0.3 part |
| 2,6-di-t-butyl-p-cresol | 0.1 part |

-continued

| Compound 18 | 0.3 part |
|---|---|
| 2-hydroxy-4-octoxy-benzophenone | 0.3 part |

Formulation 4

| Polyvinyl chloride | 100 parts |
|---|---|
| Calcium stearate | 1 part |
| Compound 7 | 0.5 part |

Formulation 5

| Polyvinyl chloride | 100 parts |
|---|---|
| Barium-cadmium laurate | 1 part |
| dioctyl phthalate | 60 parts |
| Compound 21 | 0.5 part |

In any of the formulations set forth above, the polypropylene or polyvinyl chloride can be replaced by one of the other polymers set forth supra, e.g. cellulose acetate, natural rubber, SBR rubber, EPDM rubber, butadiene-acrylonitrile rubbers, ABS terpolymer, polyethylene terephthalate, styrene modified ethylene glycol maleate-phthalate polymer, etc.

The term alkyl is intended to cover alkyl groups in general, e.g. of 1 to 18 or even 20 carbon atoms. Even higher alkyl groups, e.g. of 30 carbon atoms are included since they are operative, if available. The only disadvantage of having extremely high alkyl groups is that they reduce the percentage of phosphorus and metal, e.g. nickel in the compound and hence on a weight basis more stabilizer compound may be needed to have the same stabilizing effect. The term lower alkyl is intended to cover alkyl of 1 to 6 carbon atoms. The term cycloalkyl is intended to cover all available cycloalkyl groups. While cyclohexyl is generally preferred because compounds containing this group are readily available, the term is also inclusive of cyclopropyl, cyclobutyl, cyclopentyl, cycloheptyl, cyclooctyl or the like.

What is claimed is:

1. Organic solid polymer material normally susceptible to deterioration due to the effects of ultraviolet light containing a stabilizingly effective quantity of (A) a metal complex of a trivalent phosphorus compound, said complex having the formula

where Me is nickel, manganese, iron, molybdenum or tungsten, L is P(X)(Y)(Z) where any one or all of X, Y, and Z are O-hydrocarbyl,

where $R_{31}$ and $R_{32}$ are hydrocarbyl or hydrogen, O-hydrocarbyl

piperidyl, S hydrocarbyl, hydrocarbyl, halohydrocarbyl where the halogen has an atomic weight of 35 to 80, 2 or 3 of X, Y and Z together with P form a heterocyclic ring of 5 to 6 carbon atoms, A is an anion, m is zero or a small whole number, L' is CO, NO, CN or halogen, o is zero or a small whole number, n is a small whole number of at least 1, o + m + n is not greater than the highest coordination number of the metal.

2. An organic material according to claim 1 wherein (A) is

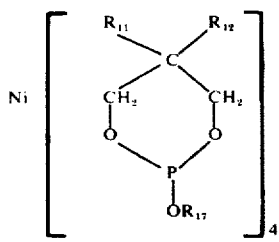

where $R_{11}$ and $R_{12}$ are hydrogen or lower alkyl and $R_{17}$ is hydrocarbyl or haloalkyl where the halogen has an atomic weight of 35 to 80.

3. An organic material according to claim 2 wherein $R_{17}$ is alkyl or cycloalkyl or halo lower alkyl.

4. An organic material according to claim 3 wherein $R_{17}$ is cyclohexyl.

5. An organic material according to claim 4 wherein $R_{11}$ and $R_{12}$ are methyl.

6. An organic material according to claim 3 wherein the polymer is a propylene polymer.

7. An organic material according to claim 2 wherein there is also included (B) another ultraviolet light stabilizer selected from the group consisting of hydroxybenzophenones, salicylates, resorcylates, benzylidene malonates, benzotriazoles, substituted acrylonitriles and metal organo complexes other than (A).

8. An organic material according to claim 2 wherein (B) is a hydroxybenzophenone.

9. An organic material according to claim 2 where (A) is used in an amount of 0.25 part per 100 parts of polymer, there is also employed 0.25 parts of 2-hydroxy-4-octoxybenzophenone per 100 parts of polymer, 0.3 parts of distearyl thiodipropionate per 100 parts of polymer, and 0.1 part of pentaerythritol tetrakis [3(3,5-di-t-butyl-4-hydroxyphenyl)] propionate per 100 parts of polymer and the polymer is polypropylene.

10. An organic material according to claim 2 wherein the polymer is selected from the group consisting of propylene polymers, ethylene polymers and vinyl chloride polymers.

11. An organic material according to claim 2 wherein the polymer is a propylene polymer and there is also included a phenolic antioxidant.

12. An organic material according to claim 2 wherein the polymer is a propylene polymer and there is also included an organic thio compound as a stabilizer.

13. An organic material according to claim 12 wherein the thio compound is an ester of a thiodipropionic acid.

14. An organic material according to claim 13 wherein there is also included a phenolic antioxidant.

* * * * *